(12) United States Patent
Jeon et al.

(10) Patent No.: US 10,746,614 B2
(45) Date of Patent: Aug. 18, 2020

(54) STRETCHABLE MULTIMODAL SENSOR AND METHOD OF FABRICATING OF THE SAME

(71) Applicant: Korea University Research and Business Foundation, Sejong Campus, Sejong-si (KR)

(72) Inventors: Sang Hun Jeon, Seoul (KR); Min Hyun Jung, Sejong-si (KR); Kung Won Rhie, Seoul (KR); Chang Jin Yun, Seoul (KR)

(73) Assignee: Korea University Research and Business Foundation, Sejong Campus, Sejong-si (KR)

( * ) Notice: Subject to any disclaimer, the term of this patent is extended or adjusted under 35 U.S.C. 154(b) by 0 days.

(21) Appl. No.: 16/134,530

(22) Filed: Sep. 18, 2018

(65) Prior Publication Data

US 2019/0086280 A1    Mar. 21, 2019

(30) Foreign Application Priority Data

Sep. 18, 2017   (KR) .................. 10-2017-0119534

(51) Int. Cl.
*G01L 1/18* (2006.01)
*G01L 1/26* (2006.01)
(Continued)

(52) U.S. Cl.
CPC .................. *G01L 1/26* (2013.01); *A61B 5/01* (2013.01); *A61B 5/02108* (2013.01);
(Continued)

(58) Field of Classification Search
CPC .... G01L 1/26; G01L 1/18; A61B 5/01; A61B 5/02108; A61B 5/02444; A61B 5/1036;
(Continued)

(56) References Cited

U.S. PATENT DOCUMENTS 4,441,973 A * 4/1984 Noguchi ............. C23C 14/0021
                                                    136/258
6,281,036 B1 * 8/2001 Niki .................... H01L 31/0322
                                                    136/262
(Continued)

FOREIGN PATENT DOCUMENTS

KR       10-1177543 B1      8/2012
KR    10-2016-0140431 A    12/2016
KR    10-2017-0008216 A     1/2017

*Primary Examiner* — Max H Noori
(74) *Attorney, Agent, or Firm* — Sughrue Mion, PLLC

(57) ABSTRACT

A stretchable multimode sensor and a method of fabricating the same are provided. The stretchable multimode sensor may include a substrate which is formed of a flexible material and includes a pressure sensor area, an optical sensor area, a temperature sensor area and a switching element area, a pressure sensor which is disposed on the pressure sensor area and includes an amorphous metal, an optical sensor which is disposed on the optical sensor area and includes an amorphous metal, and a temperature sensor which is disposed on the temperature sensor area and includes an amorphous metal, and a switching element which is disposed on the switching element area and includes an amorphous metal.

7 Claims, 38 Drawing Sheets
(23 of 38 Drawing Sheet(s) Filed in Color)

(51) Int. Cl.
*G01J 1/42* (2006.01)
*G01K 7/16* (2006.01)
*A61B 5/00* (2006.01)
*A61B 5/021* (2006.01)
*G01J 1/04* (2006.01)
*A61B 5/103* (2006.01)
*A61B 5/01* (2006.01)
*A61B 5/024* (2006.01)
*G01K 7/18* (2006.01)
*G01J 1/44* (2006.01)

(52) U.S. Cl.
CPC ........ *A61B 5/02444* (2013.01); *A61B 5/1036* (2013.01); *A61B 5/6801* (2013.01); *G01J 1/0403* (2013.01); *G01J 1/42* (2013.01); *G01K 7/16* (2013.01); *G01K 7/186* (2013.01); *G01L 1/18* (2013.01); *A61B 2562/0247* (2013.01); *A61B 2562/0261* (2013.01); *A61B 2562/0271* (2013.01); *A61B 2562/12* (2013.01); *A61B 2562/164* (2013.01); *G01J 2001/446* (2013.01)

(58) Field of Classification Search
CPC .......... A61B 5/6801; A61B 2562/0247; A61B 2562/0261; A61B 2562/0271; A61B 2562/12; A61B 2562/164; G01J 1/0403; G01J 1/42; G01J 2001/446; G01K 7/16; G01K 7/186
USPC .................................................... 73/862.541
See application file for complete search history.

(56) References Cited

U.S. PATENT DOCUMENTS

| | | | | |
|---|---|---|---|---|
| 7,678,710 | B2 * | 3/2010 | Chua | H01J 37/32082 438/784 |
| 7,837,838 | B2 * | 11/2010 | Chua | C23C 14/10 204/192.22 |
| 2003/0000827 | A1 * | 1/2003 | Lee | C23C 14/34 204/192.15 |
| 2007/0049048 | A1 * | 3/2007 | Rauf | H01J 37/3266 438/775 |
| 2012/0065072 | A1 * | 3/2012 | Hays | G01R 33/035 505/162 |
| 2014/0191618 | A1 * | 7/2014 | Kijima | H01L 41/257 310/357 |
| 2016/0226065 | A1 * | 8/2016 | Karabacak | H01M 4/485 |
| 2019/0301004 | A1 * | 10/2019 | Mayet | C23C 14/5873 |

* cited by examiner

【FIG. 1】
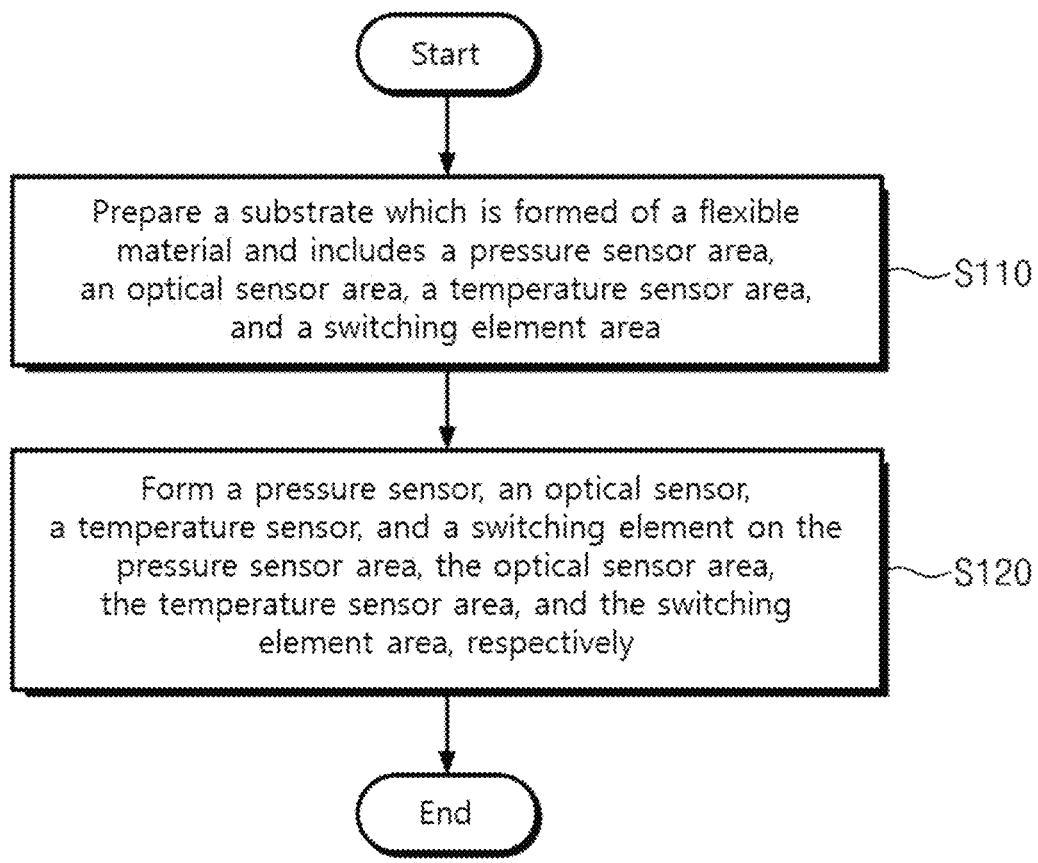
【FIG. 2】
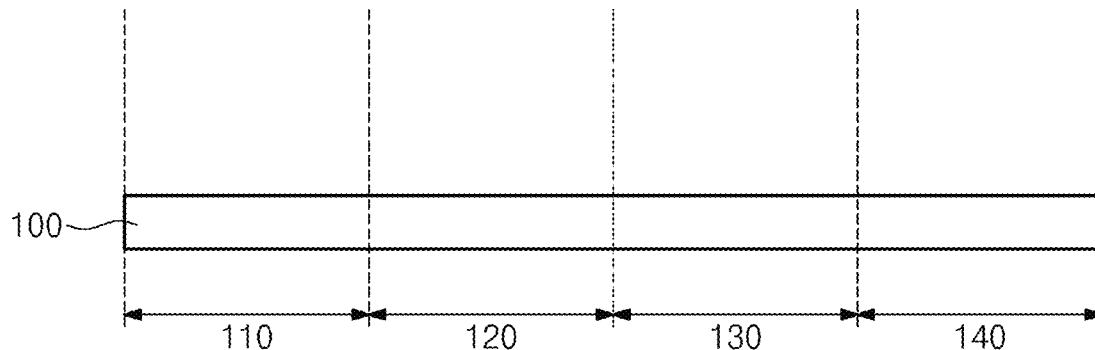

[FIG. 3]
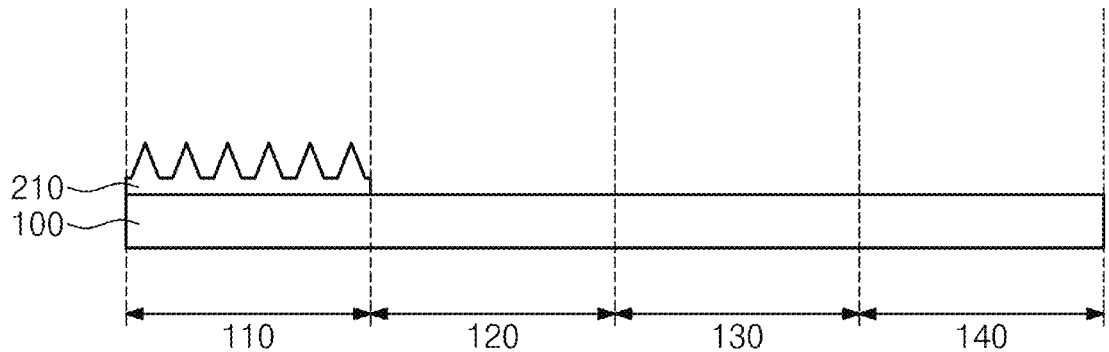
[FIG. 4]
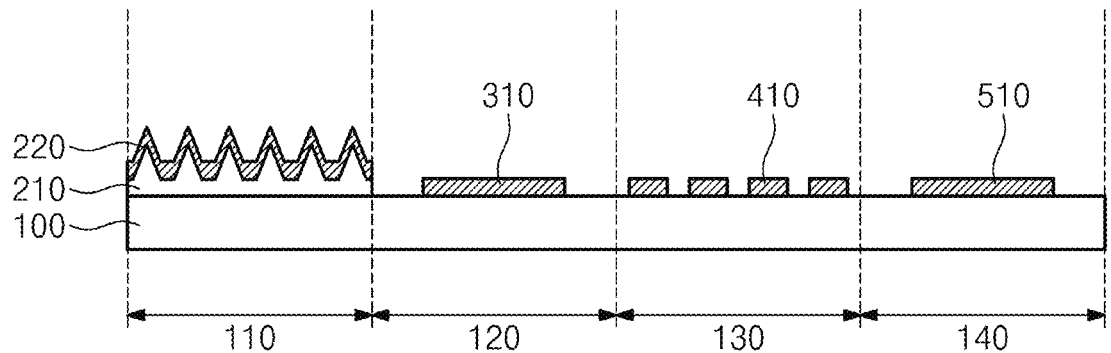
[FIG. 5]
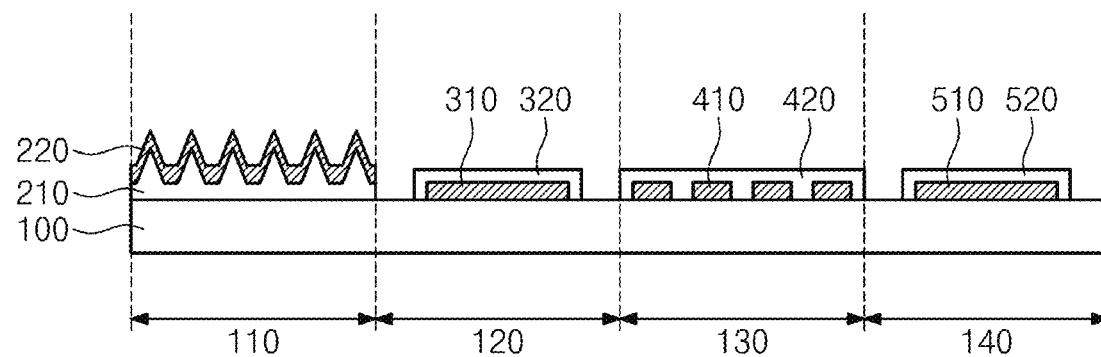

[FIG. 6]
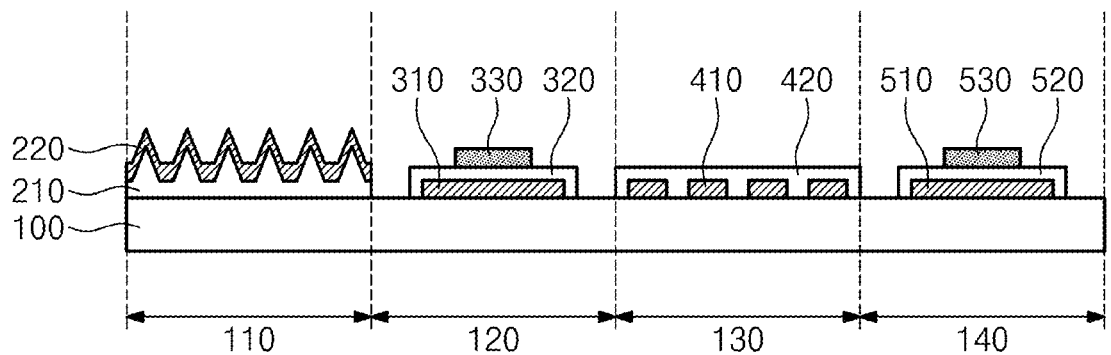
[FIG. 7]
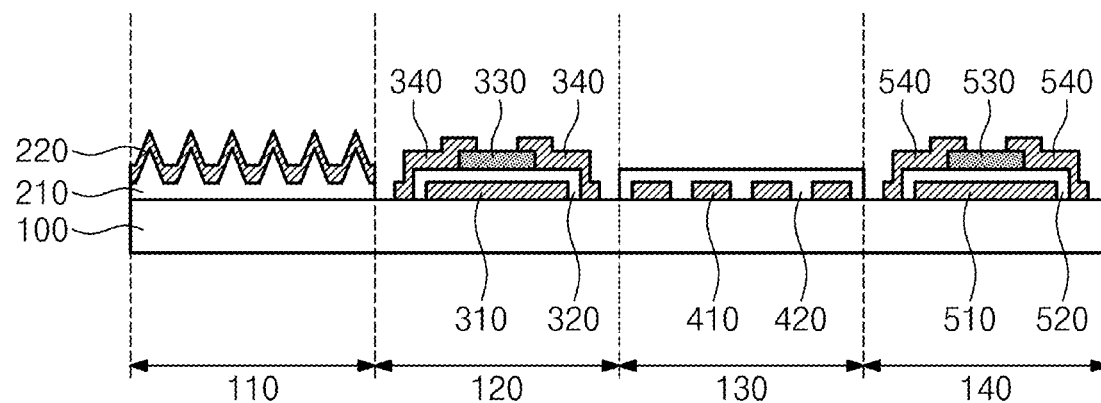

[FIG. 8]
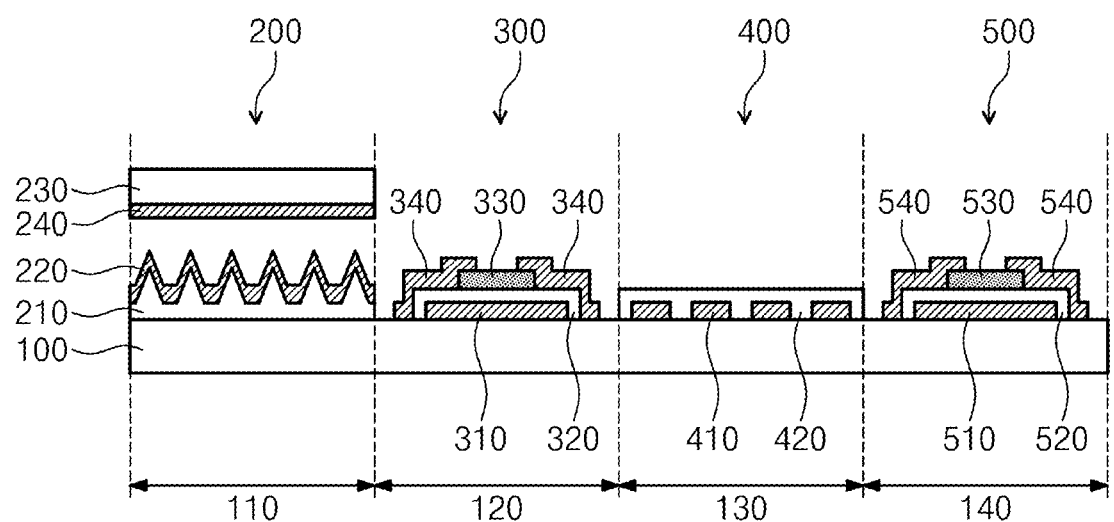

【FIG. 9】
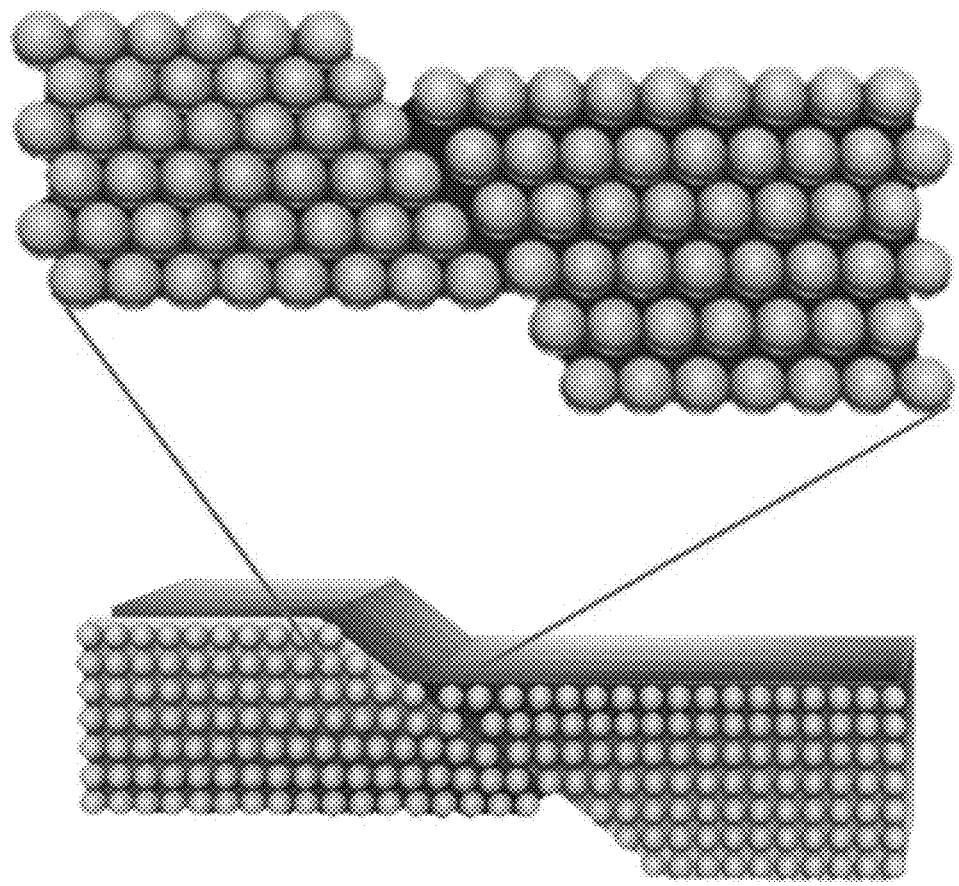

[FIG. 10]
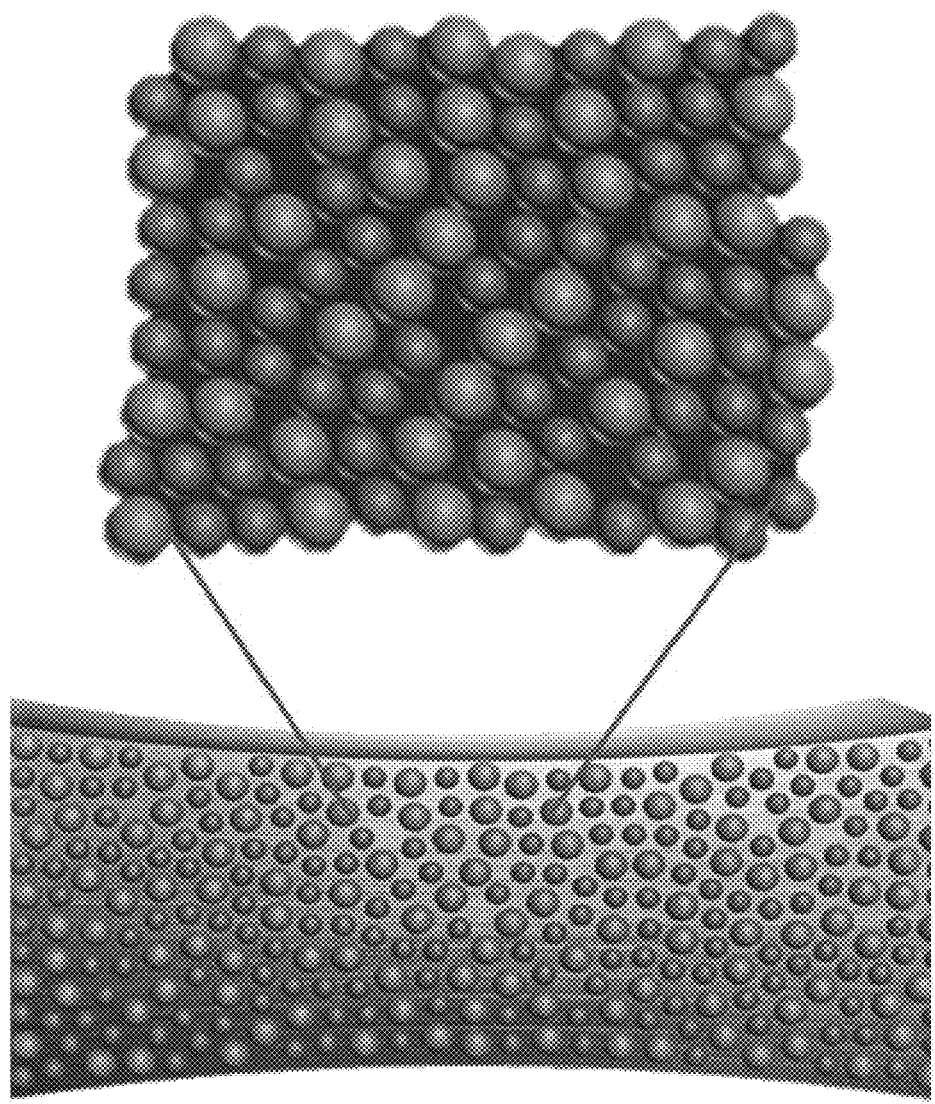

[FIG. 11]
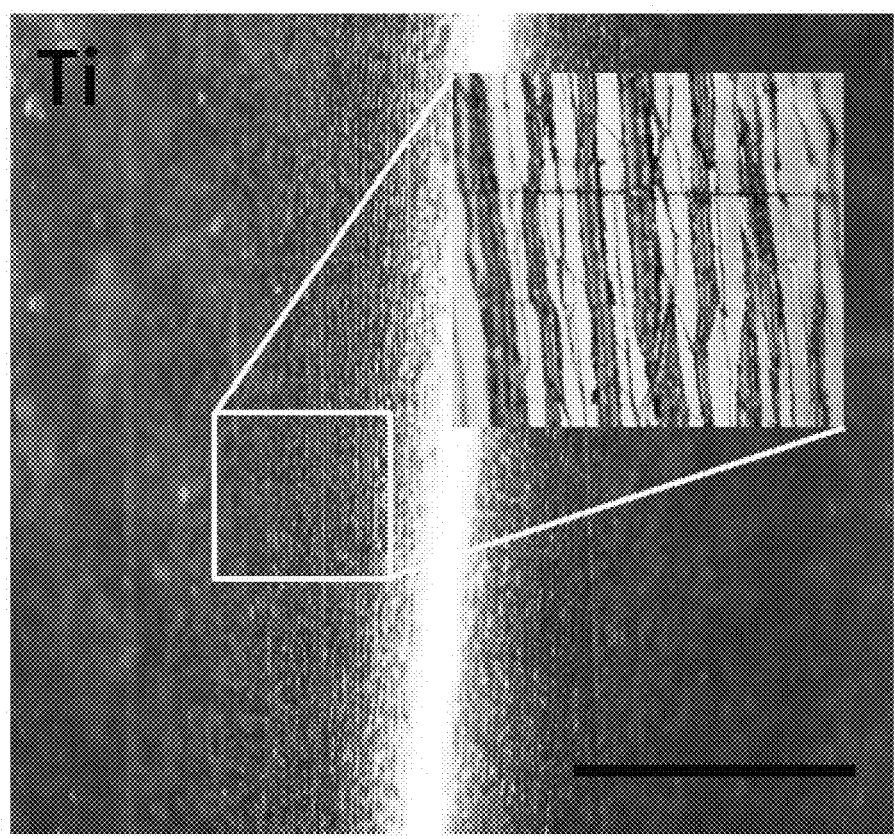

[FIG. 12]
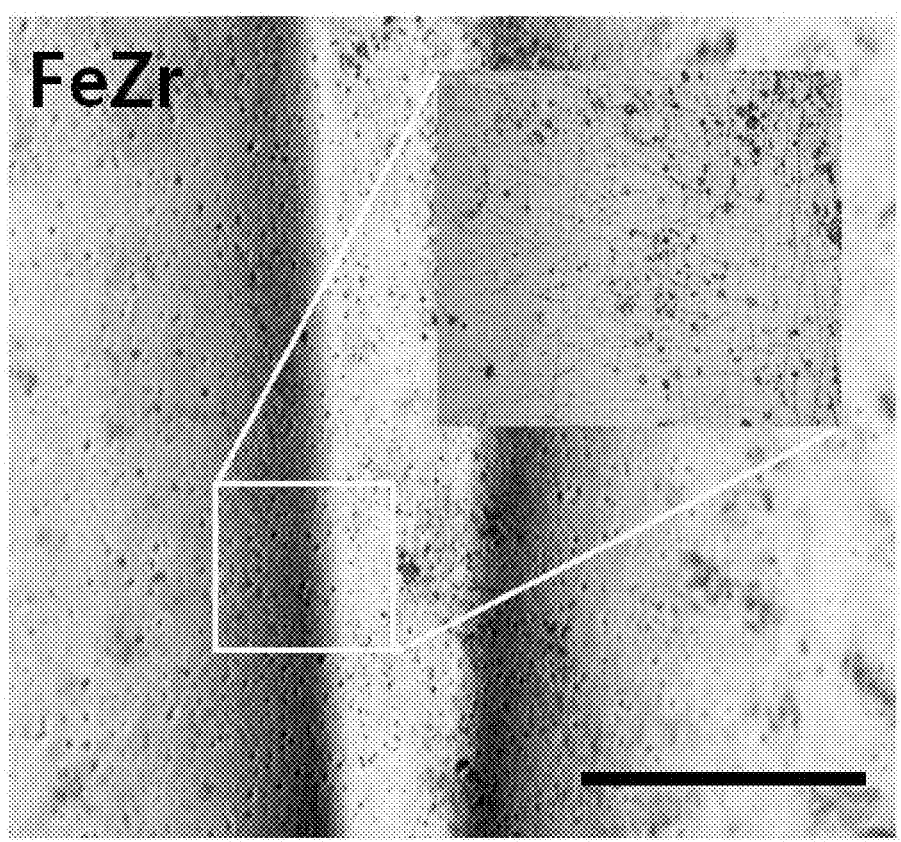

[FIG. 13]
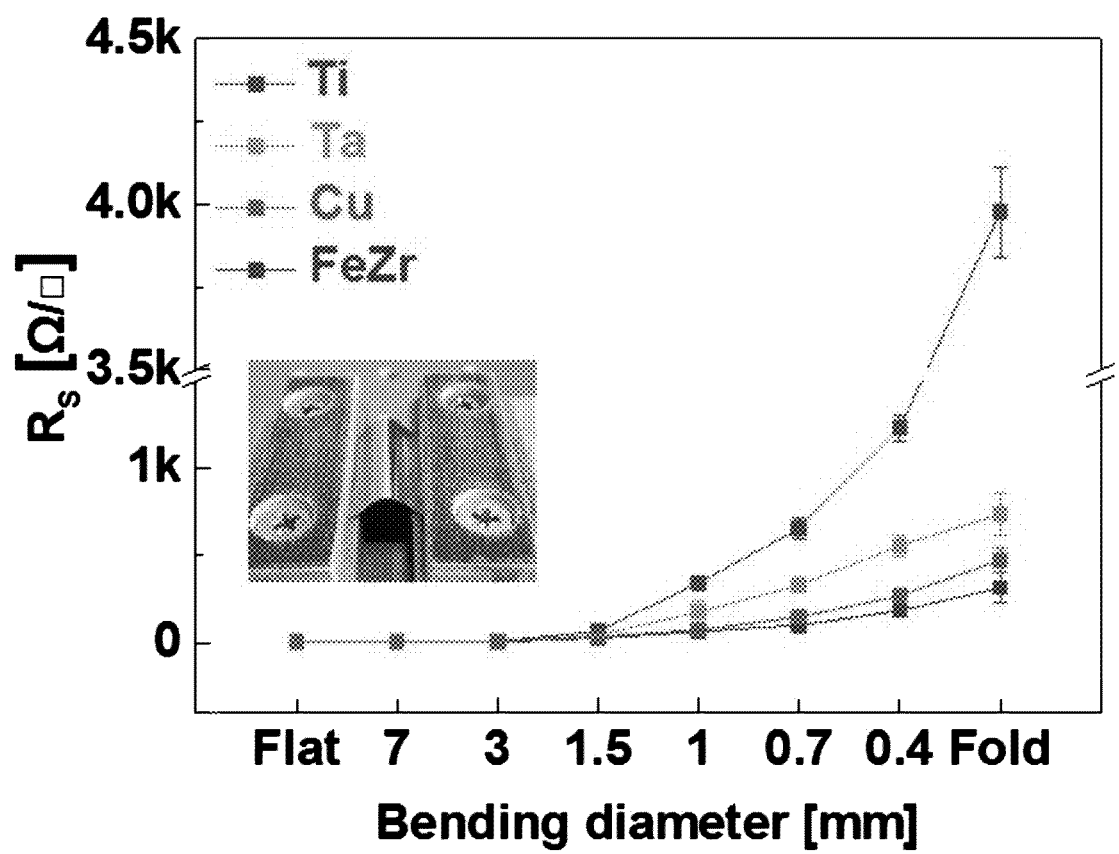

[FIG. 14]
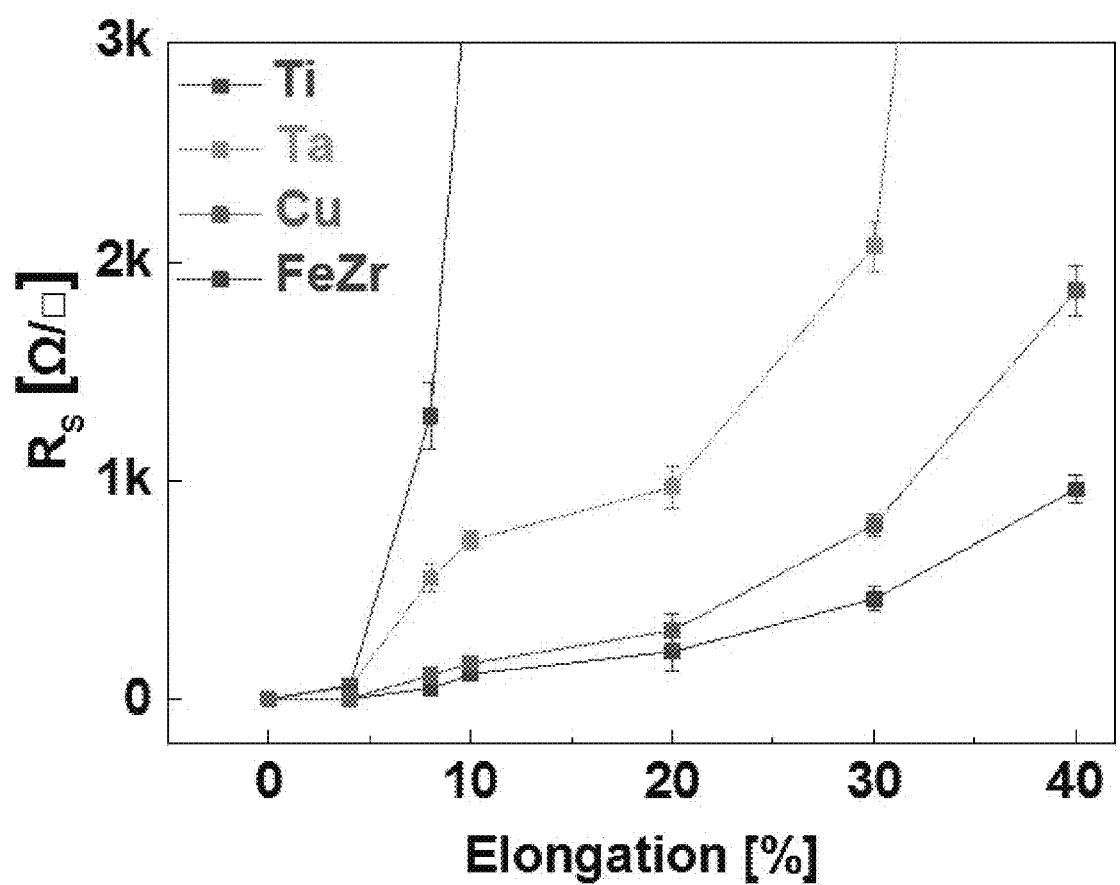

[FIG. 15]
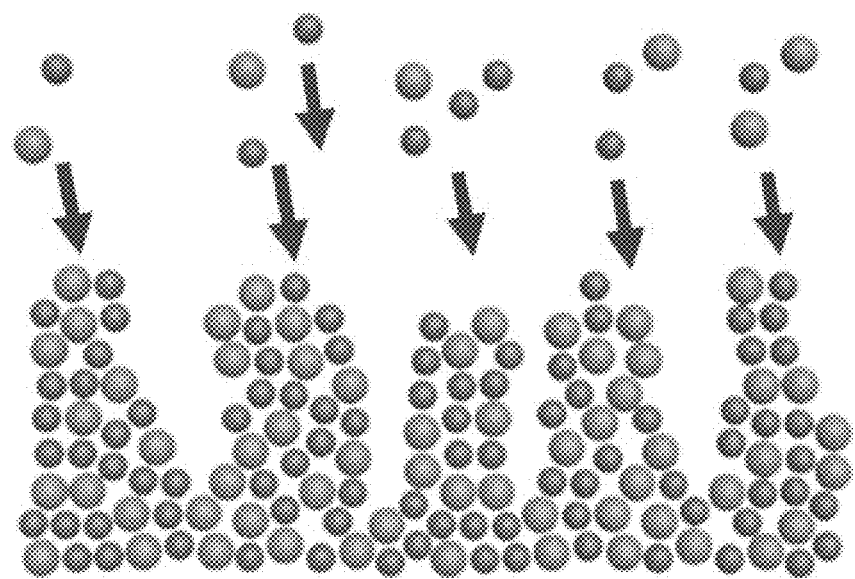

[FIG. 16]
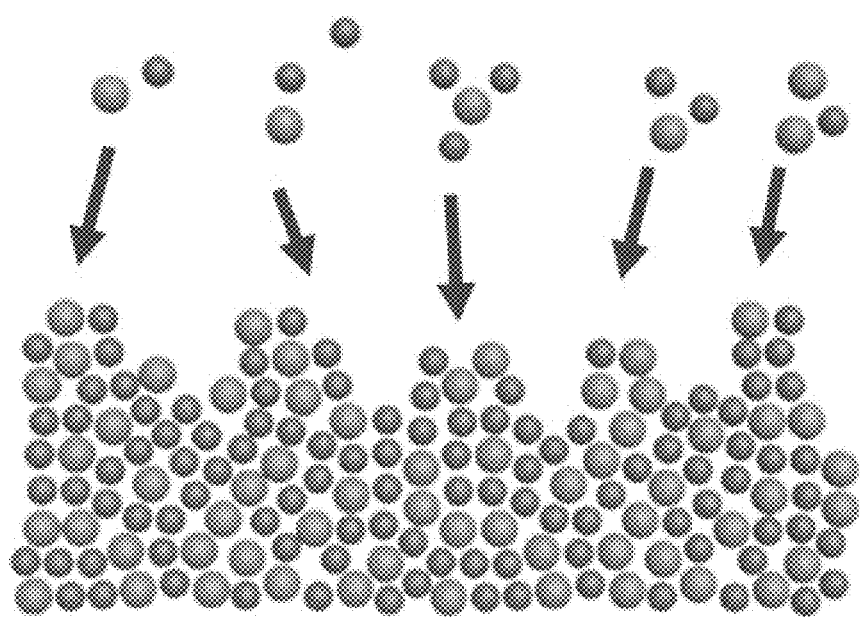

[FIG. 17]
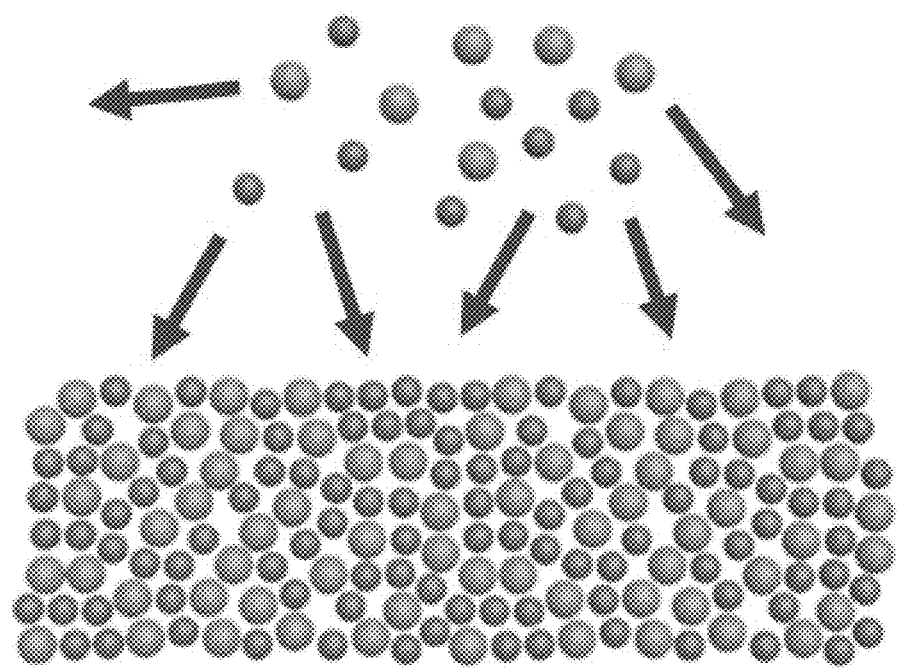

[FIG. 18]
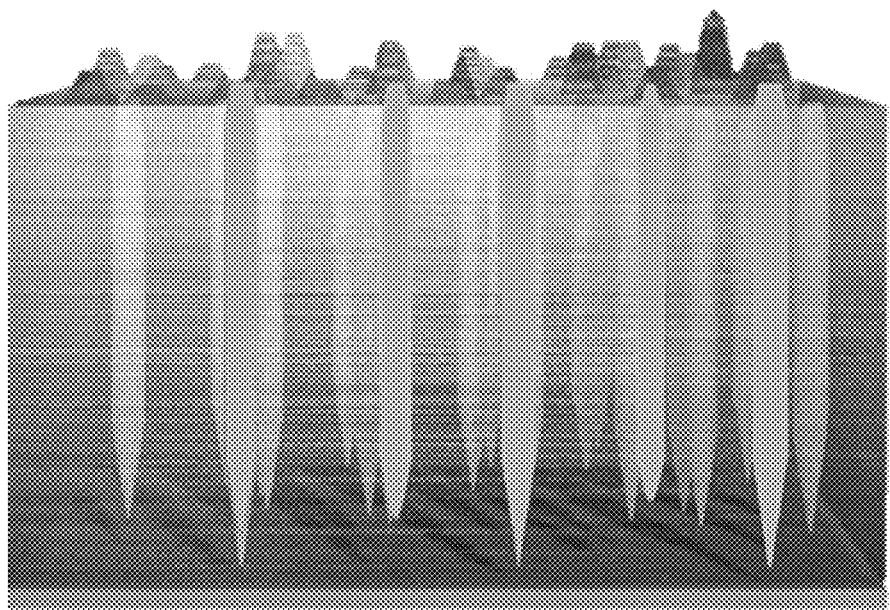

[FIG. 19]
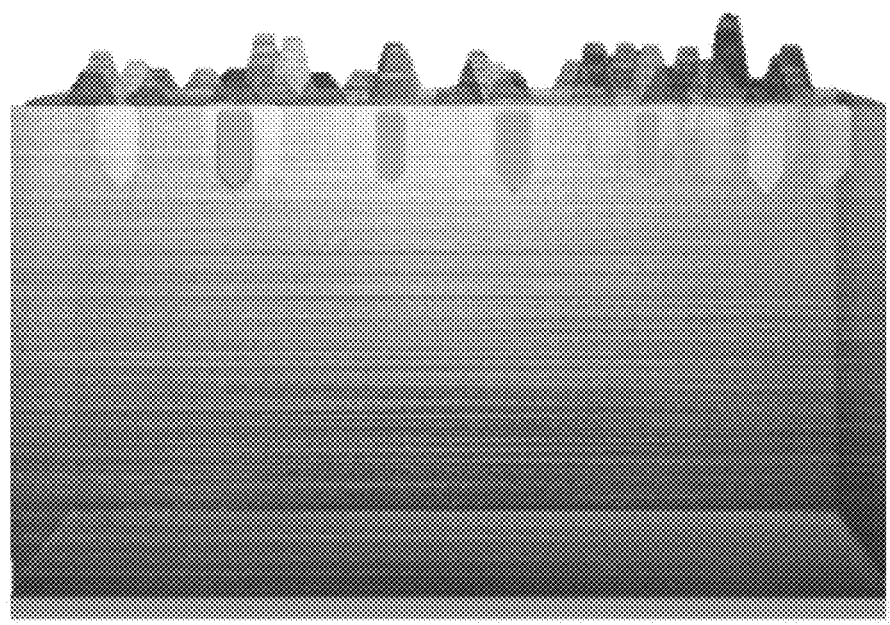

[FIG. 20]
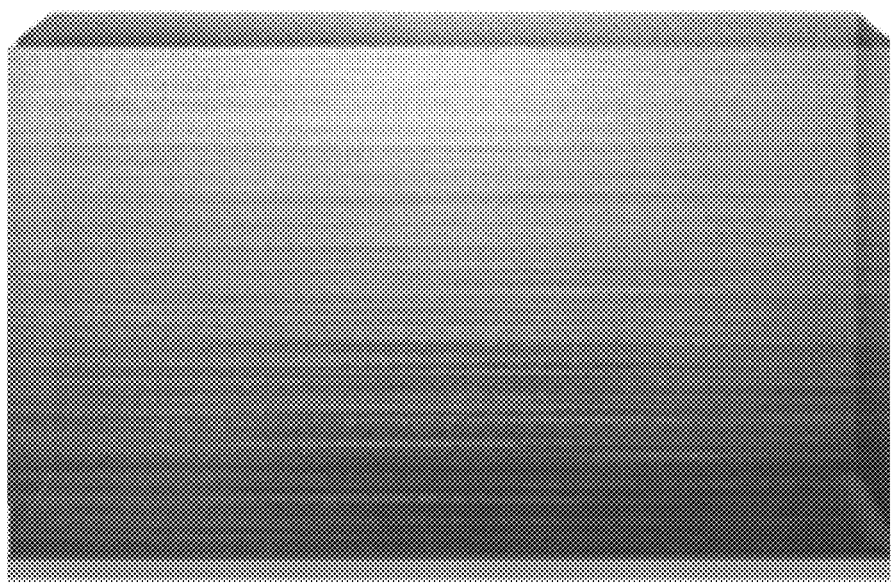

[FIG. 21]
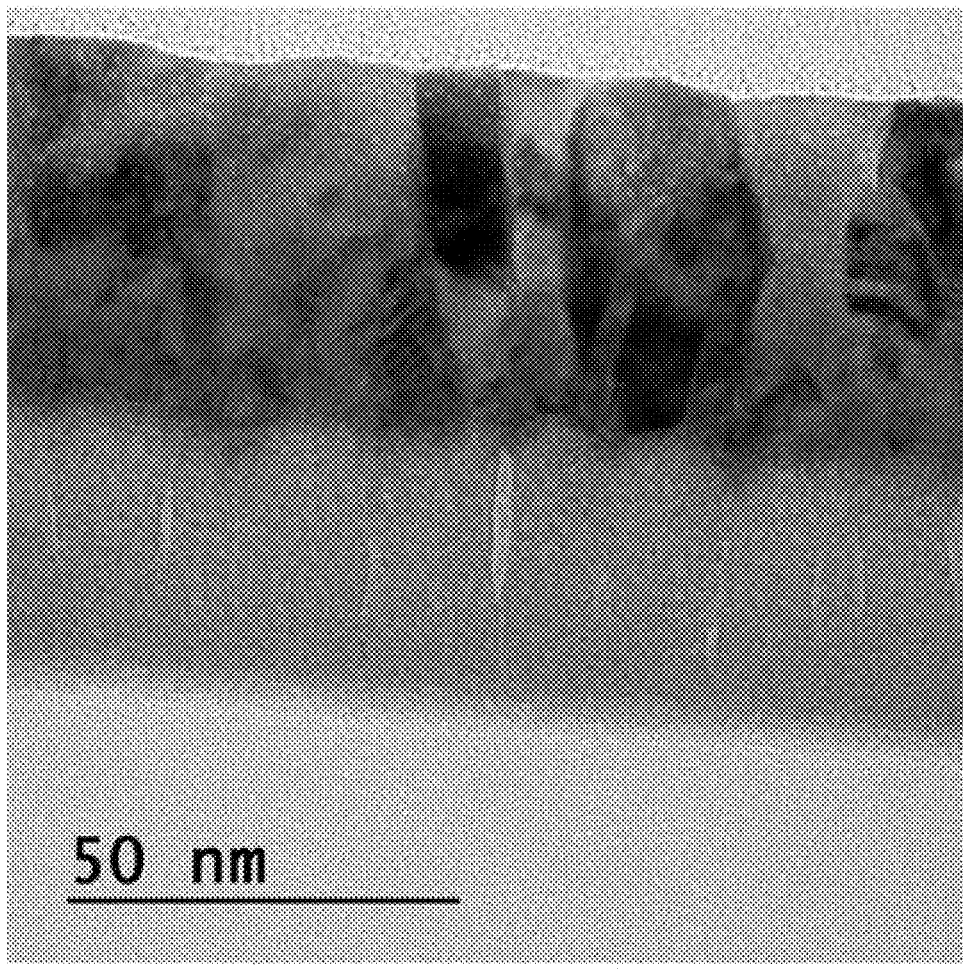

[FIG. 22]
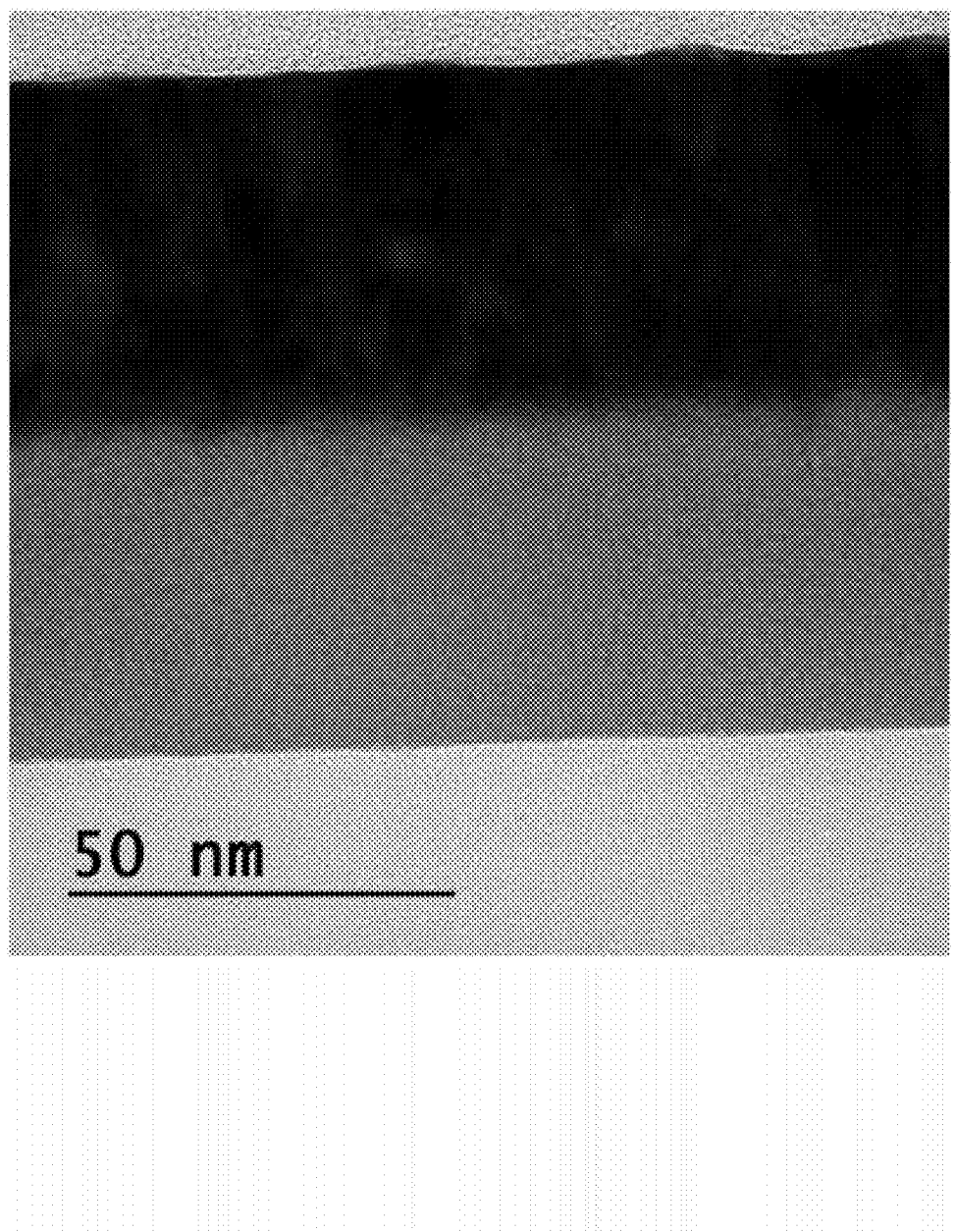

[FIG. 23]
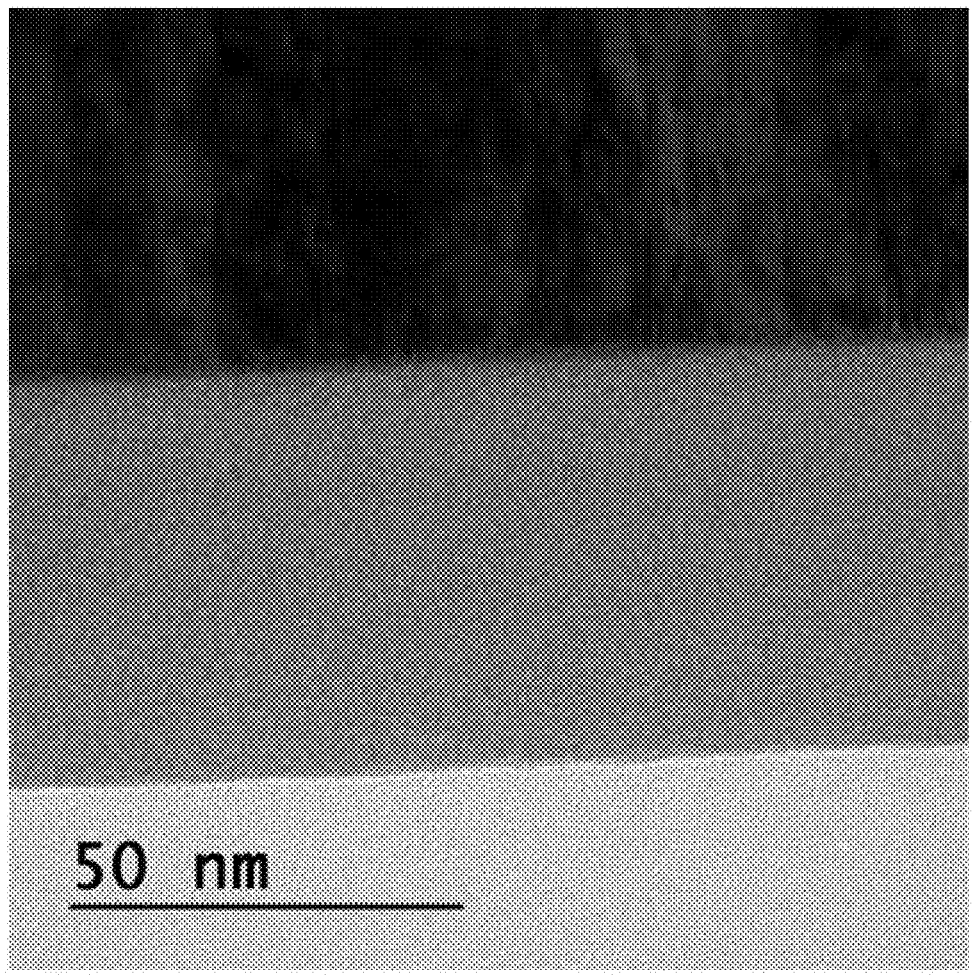

[FIG. 24]
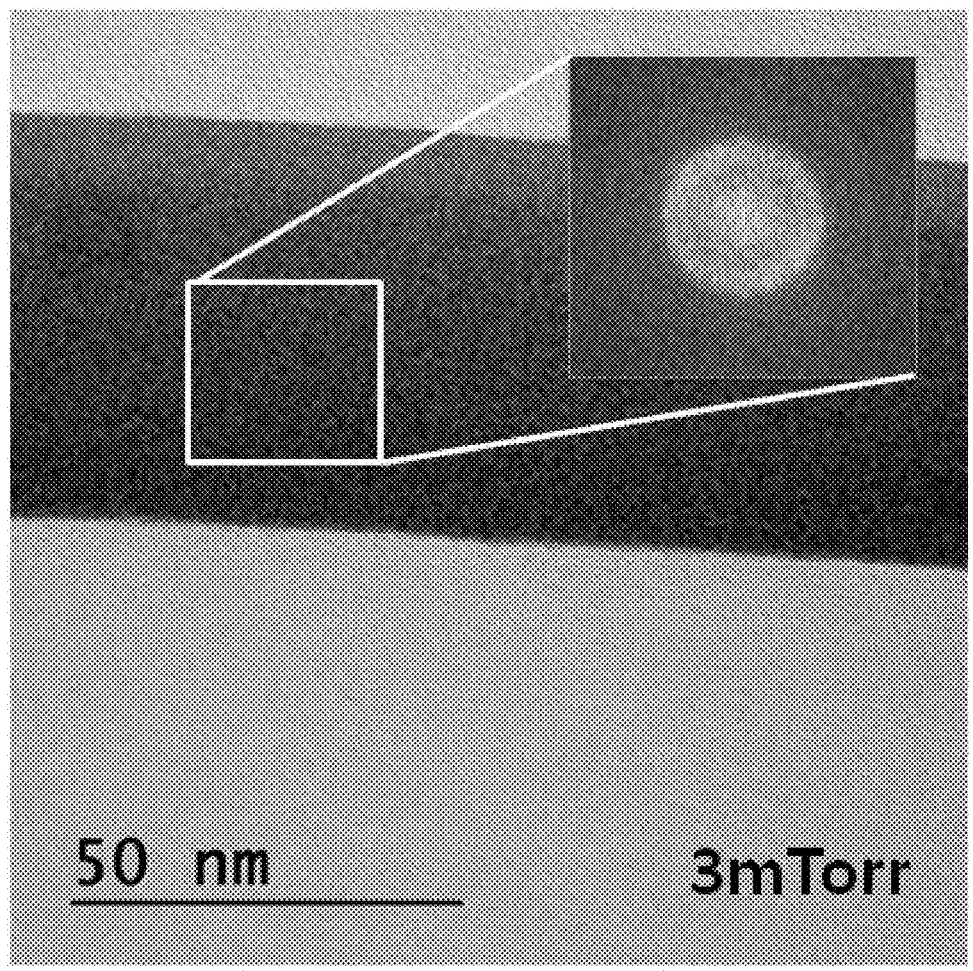

[FIG. 25]
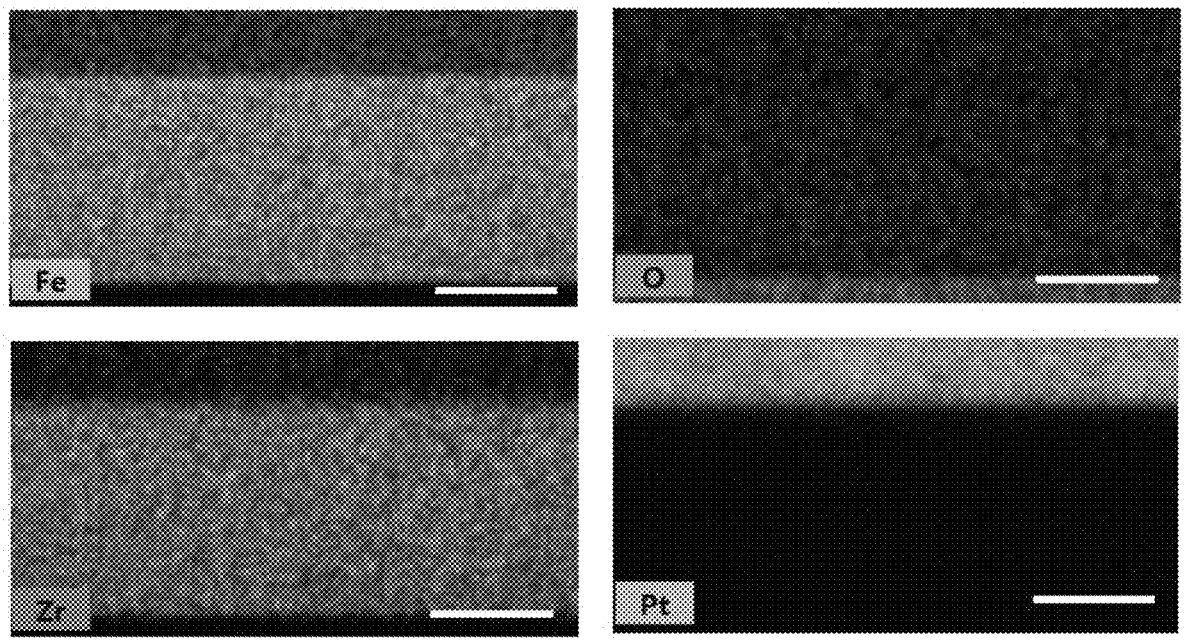

[FIG. 26]
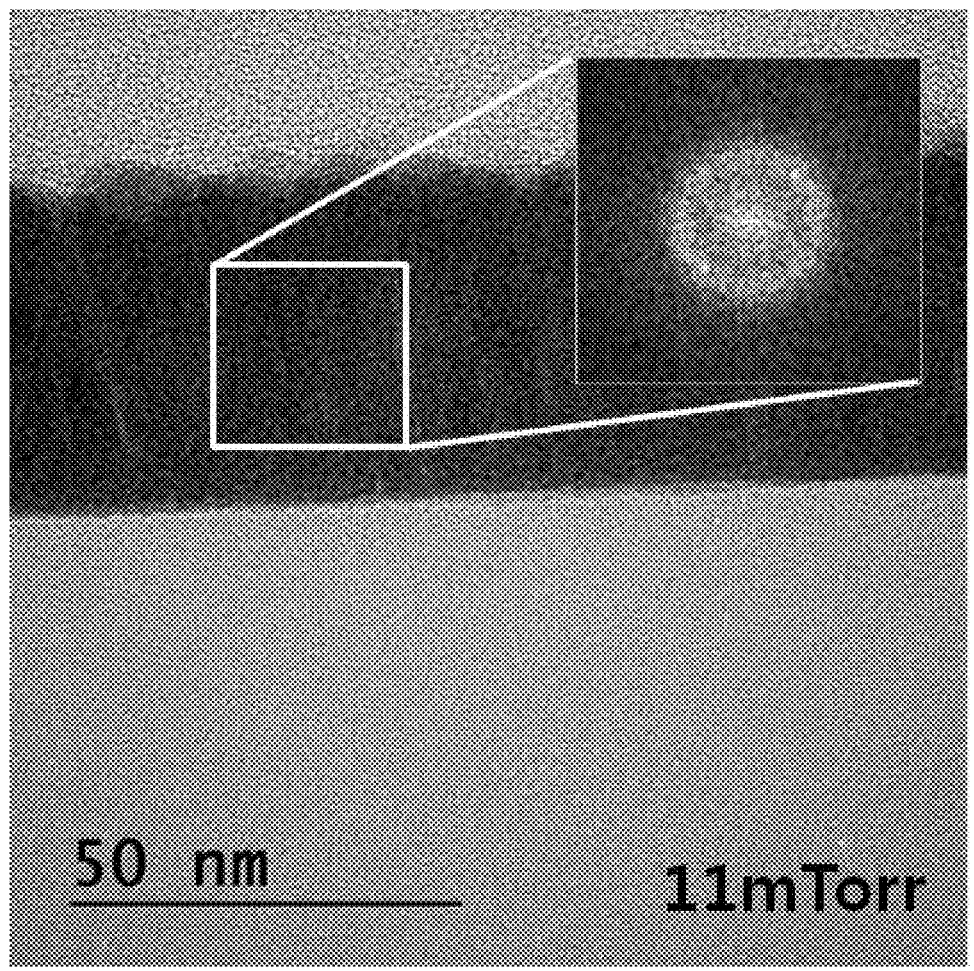

[FIG. 27]
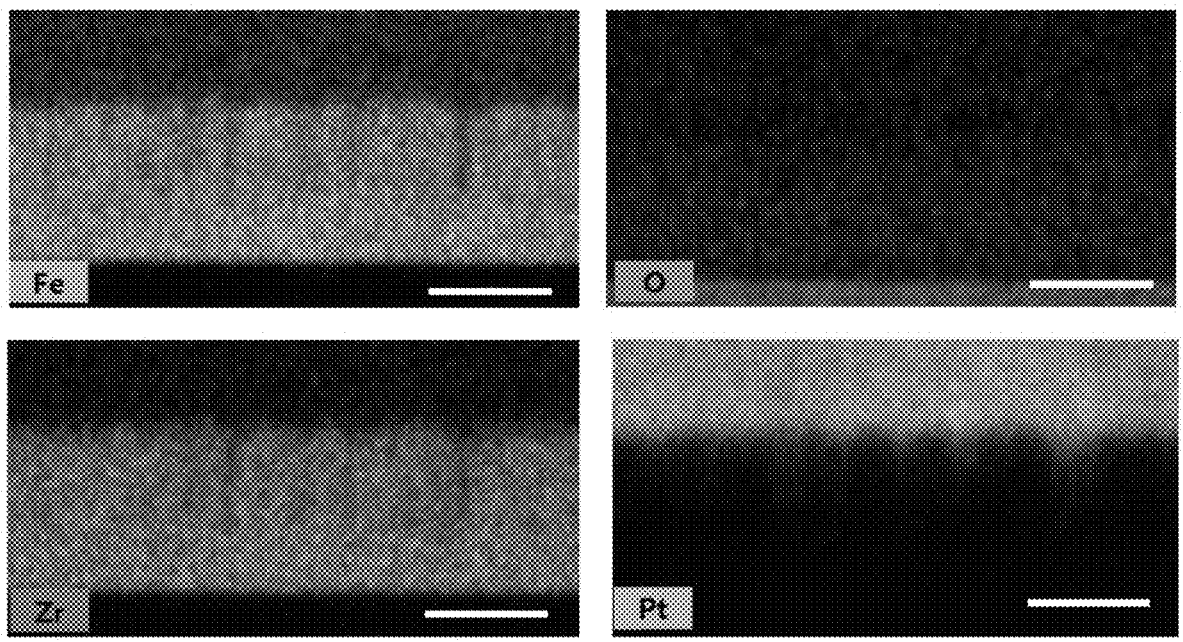

[FIG. 28]
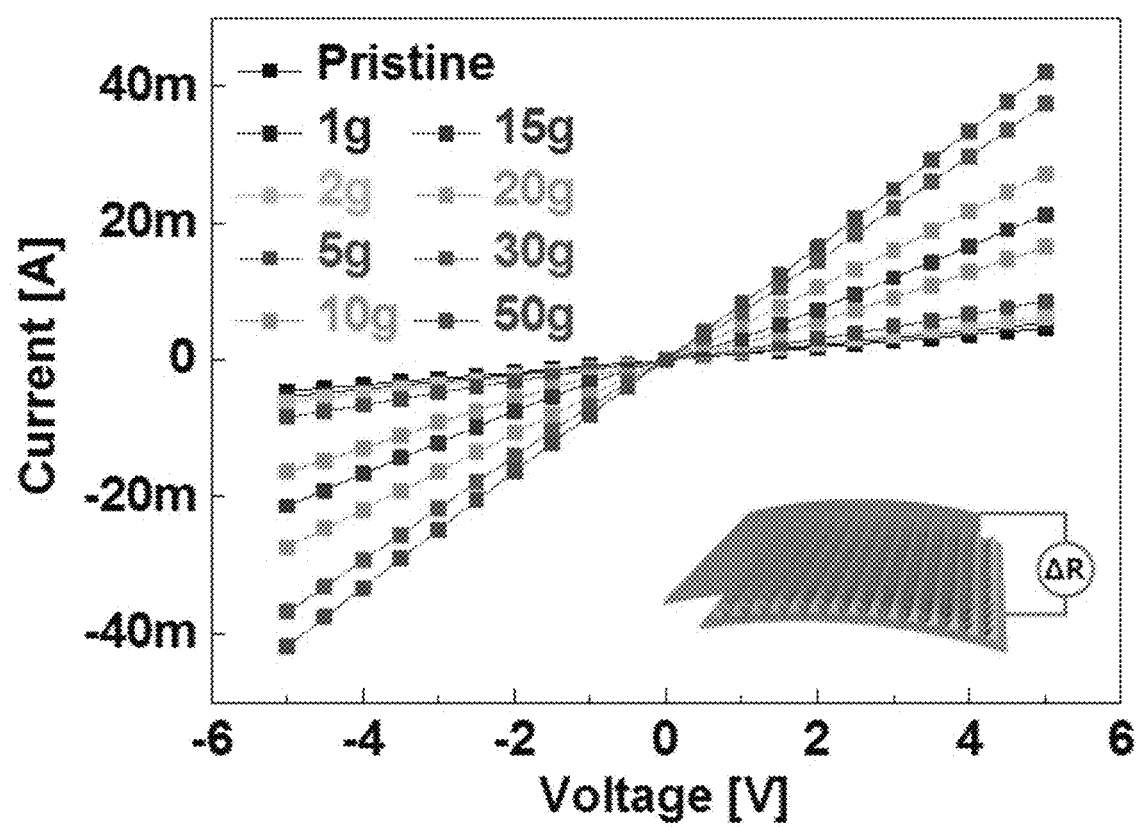

[FIG. 29]
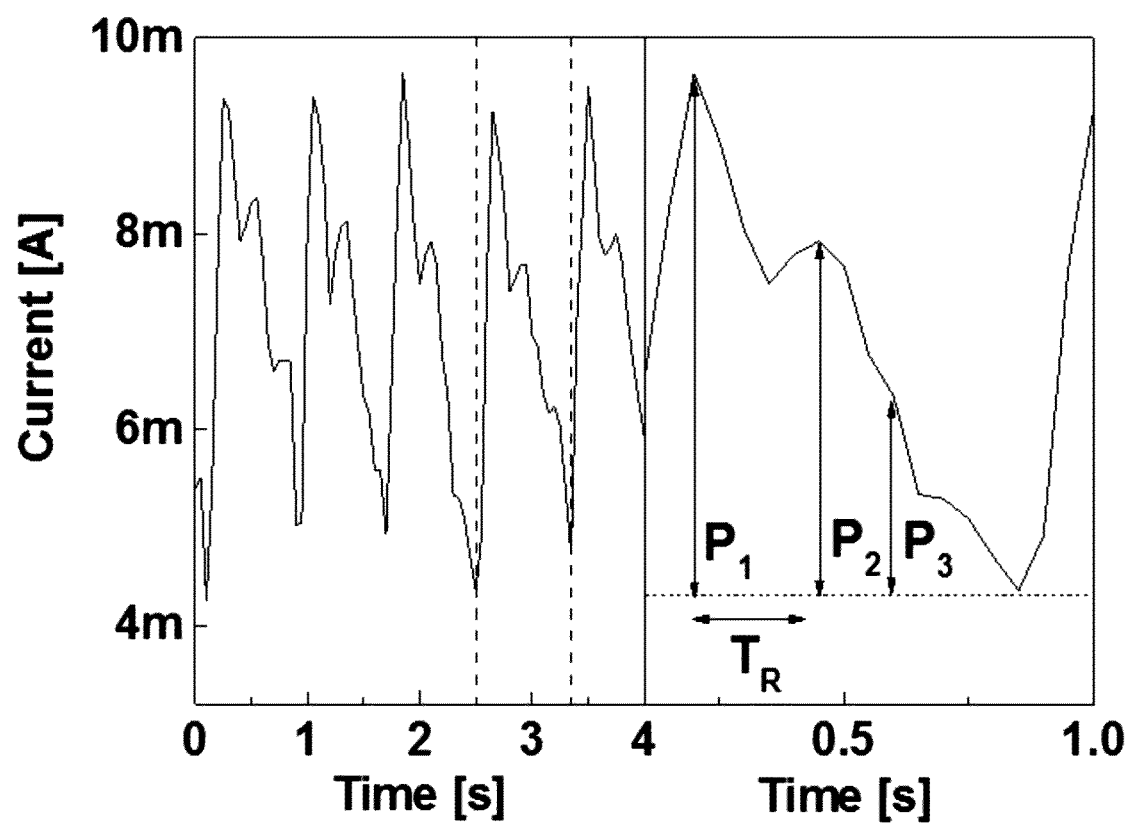

[FIG. 30]
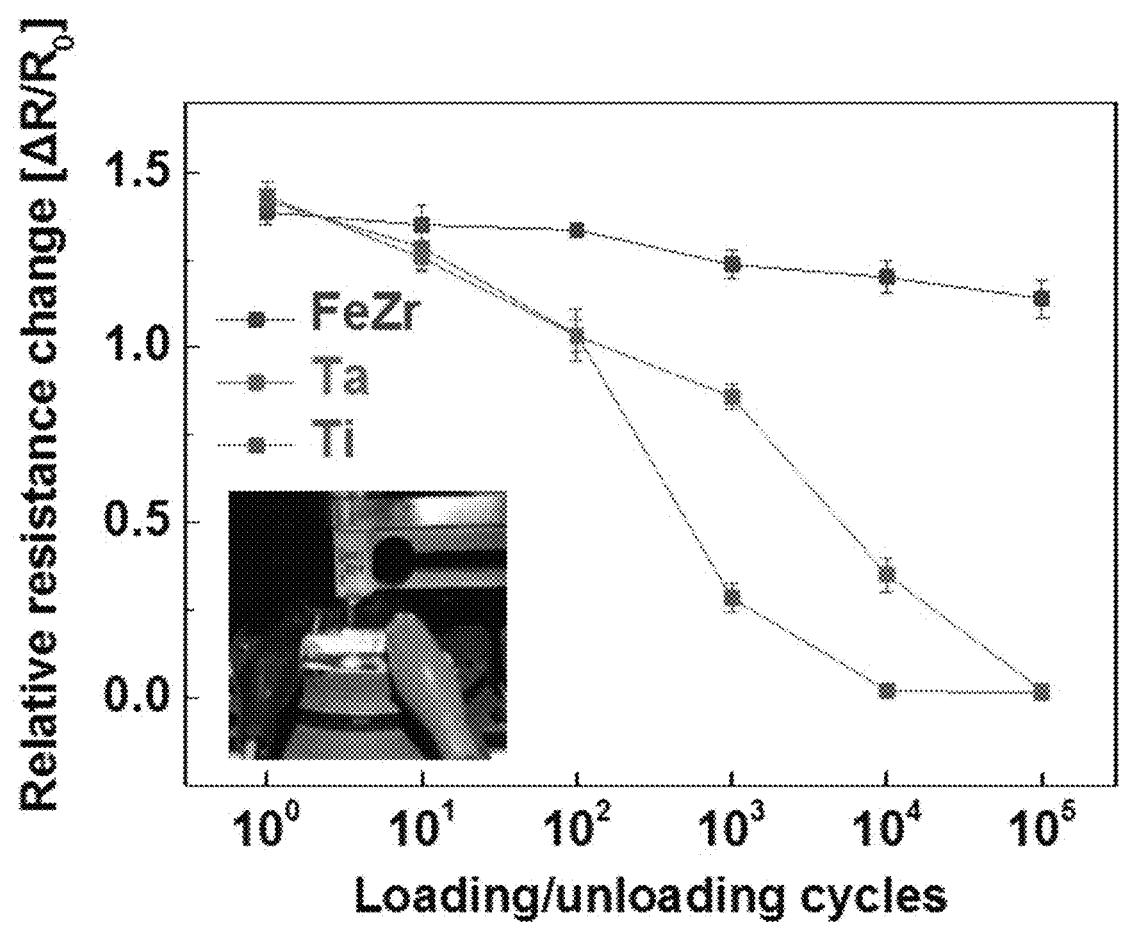

[FIG. 31]
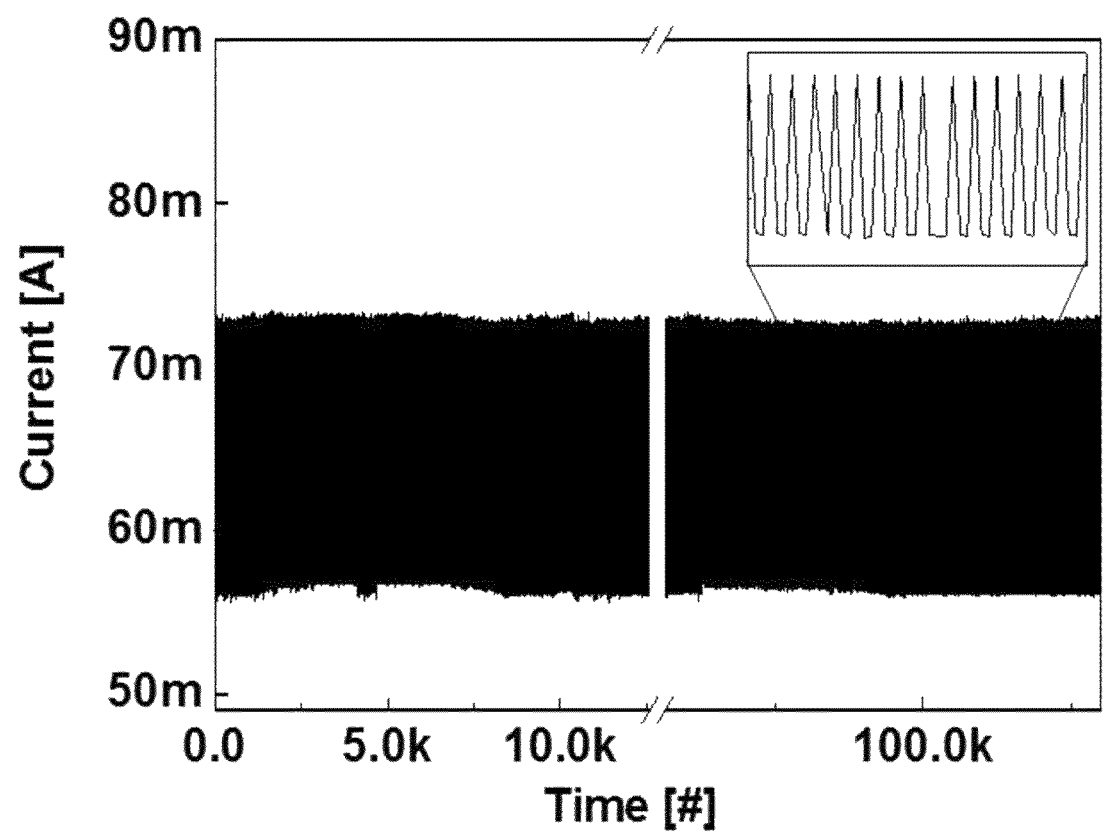

[FIG. 32]
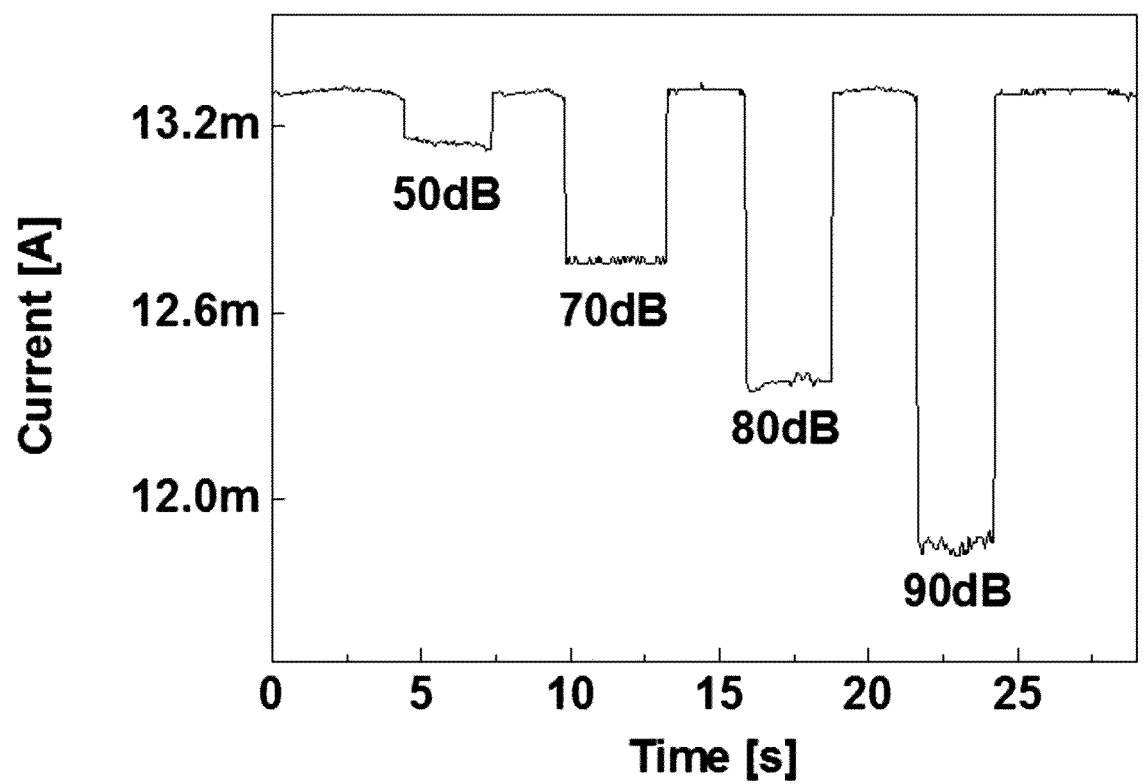

[FIG. 33]
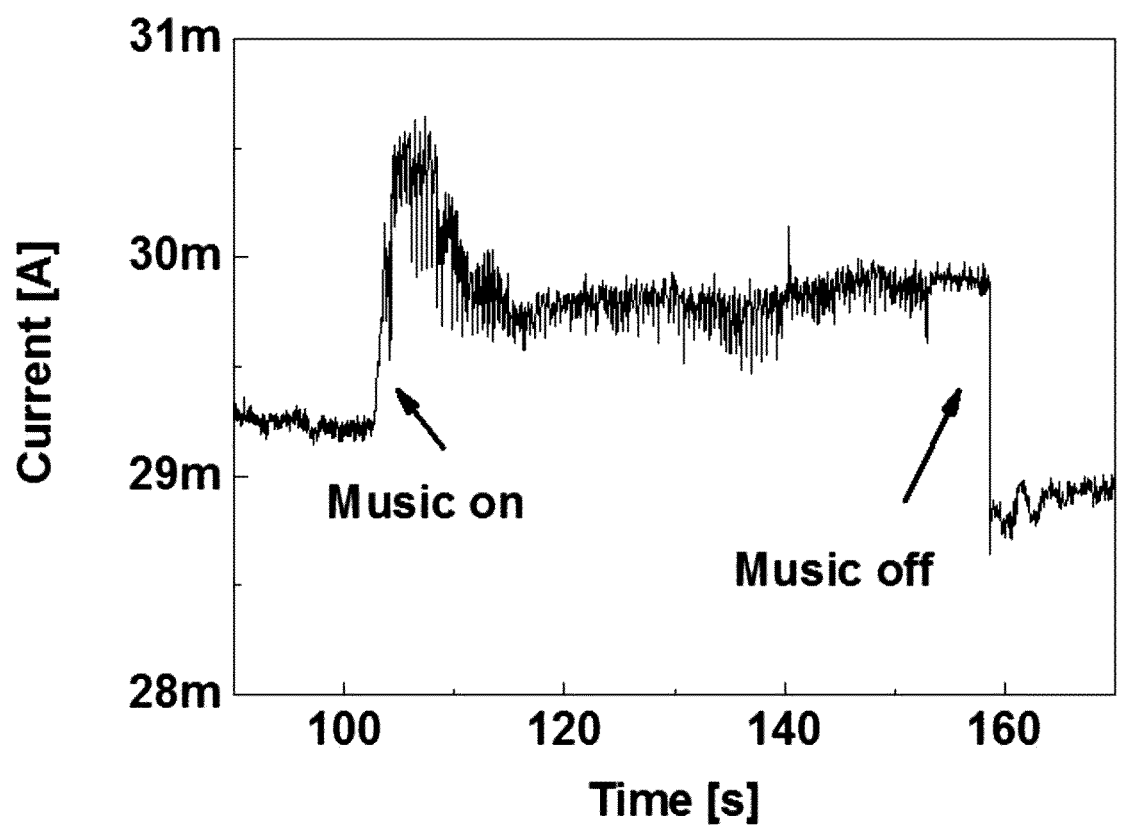

[FIG. 34]
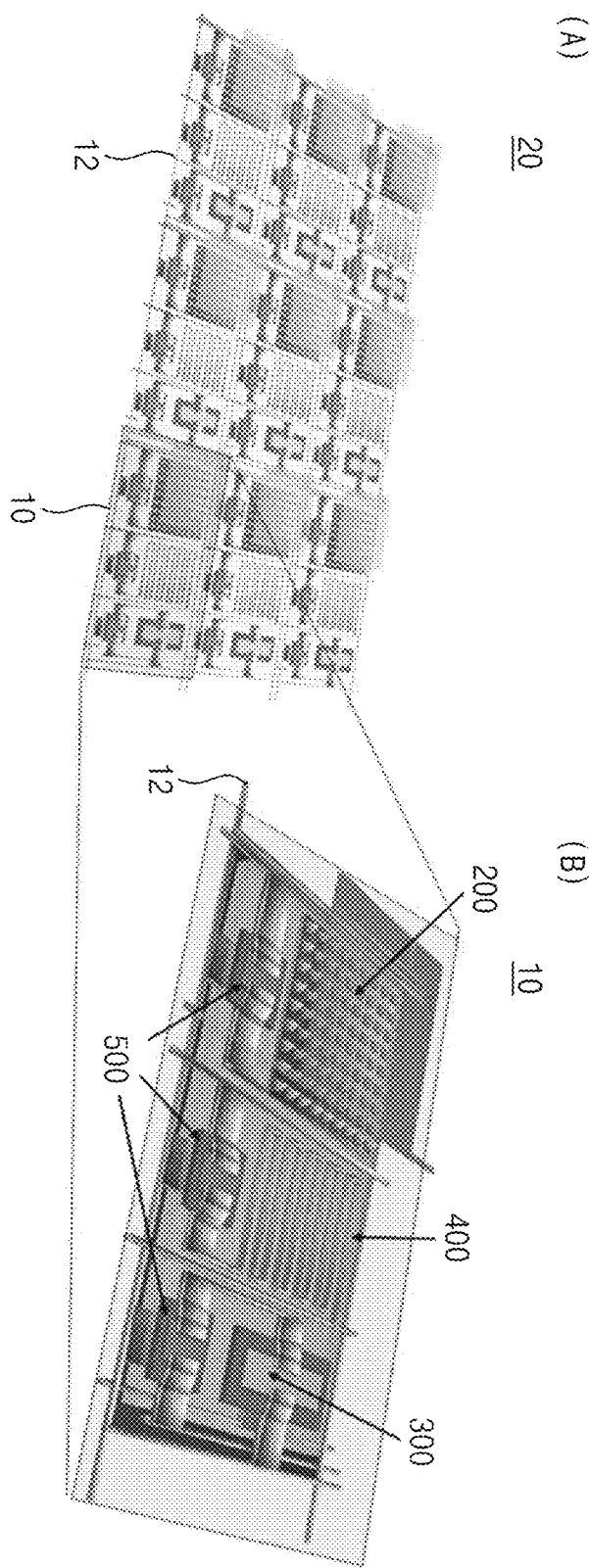

[FIG. 35]
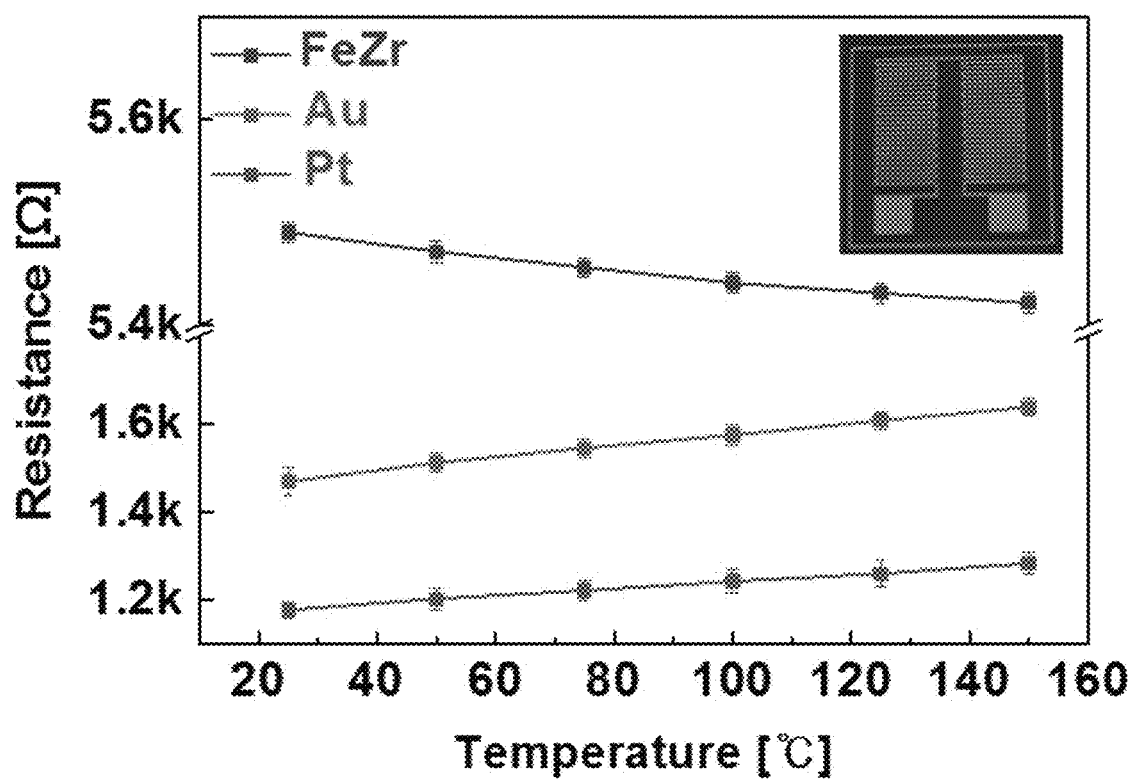

[FIG. 36]
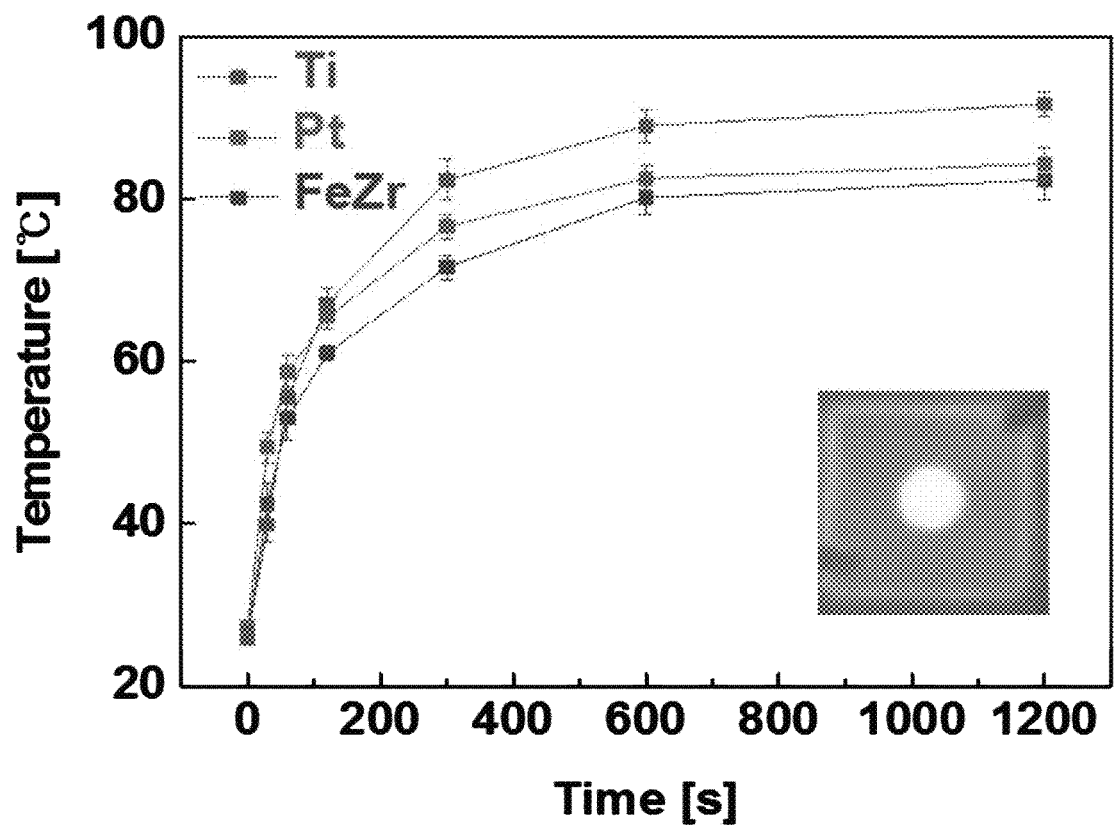

[FIG. 37]
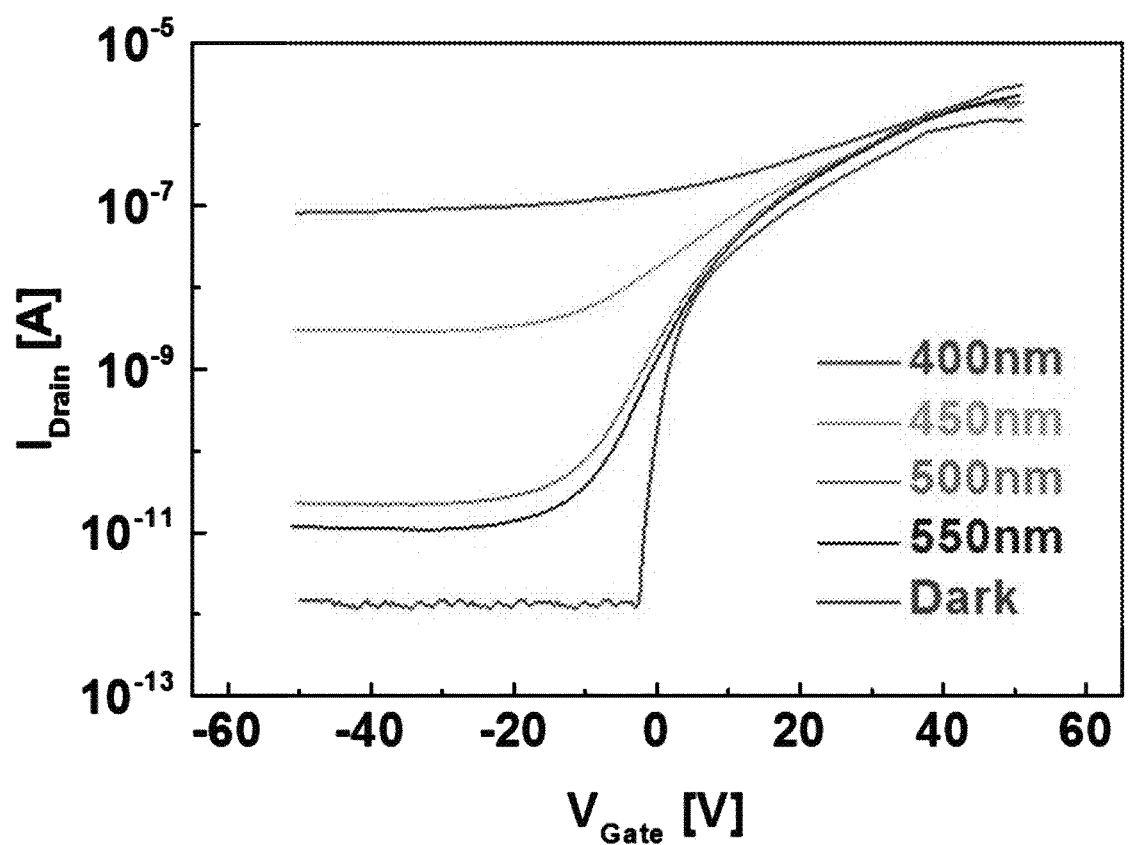

[FIG. 38]
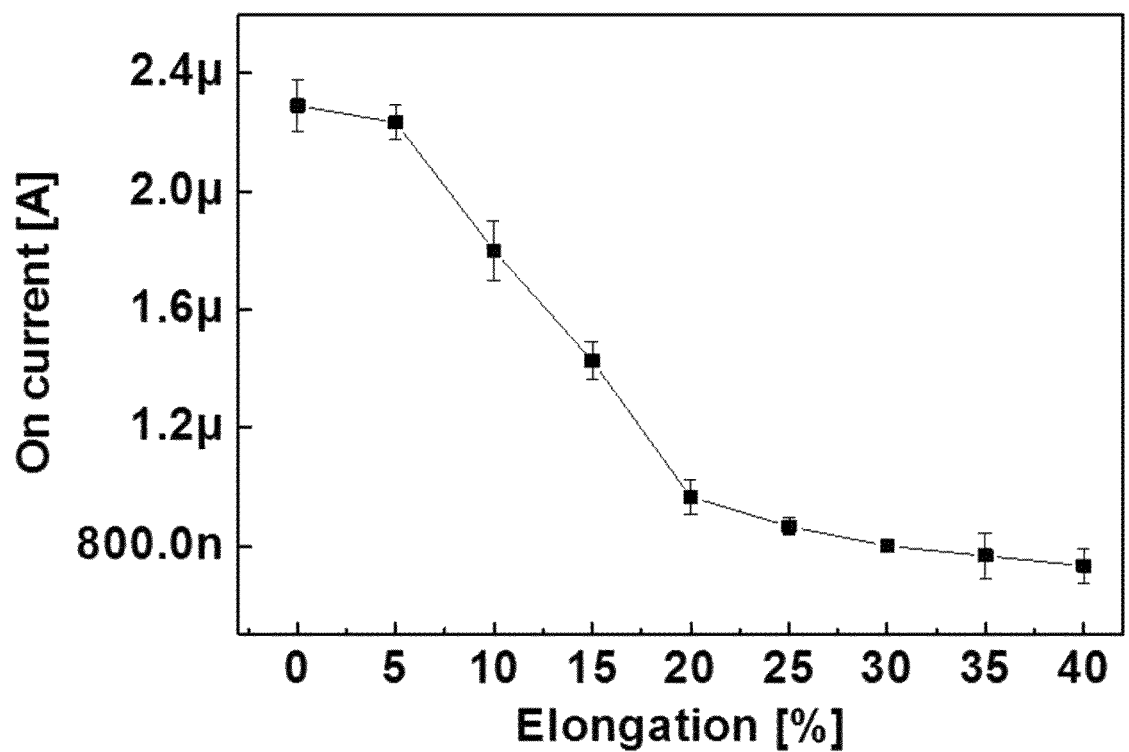

[FIG. 39]
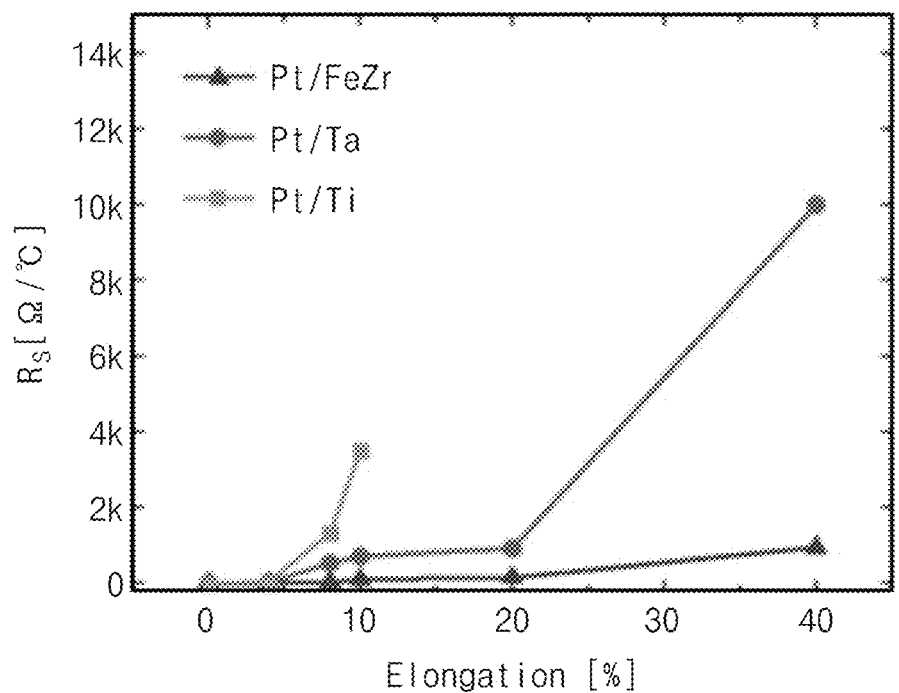
[FIG. 40]
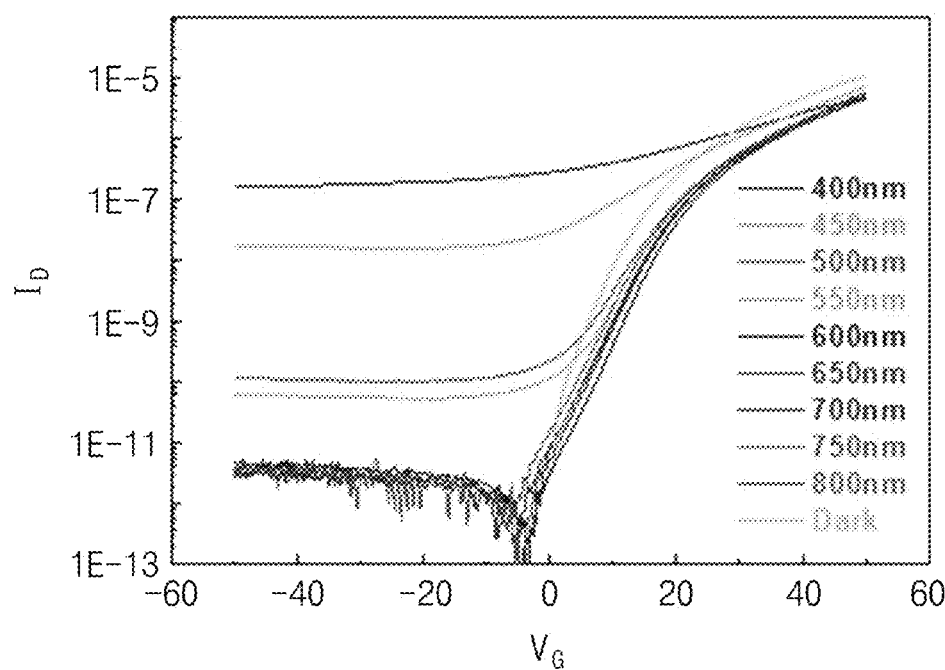

[FIG. 41]
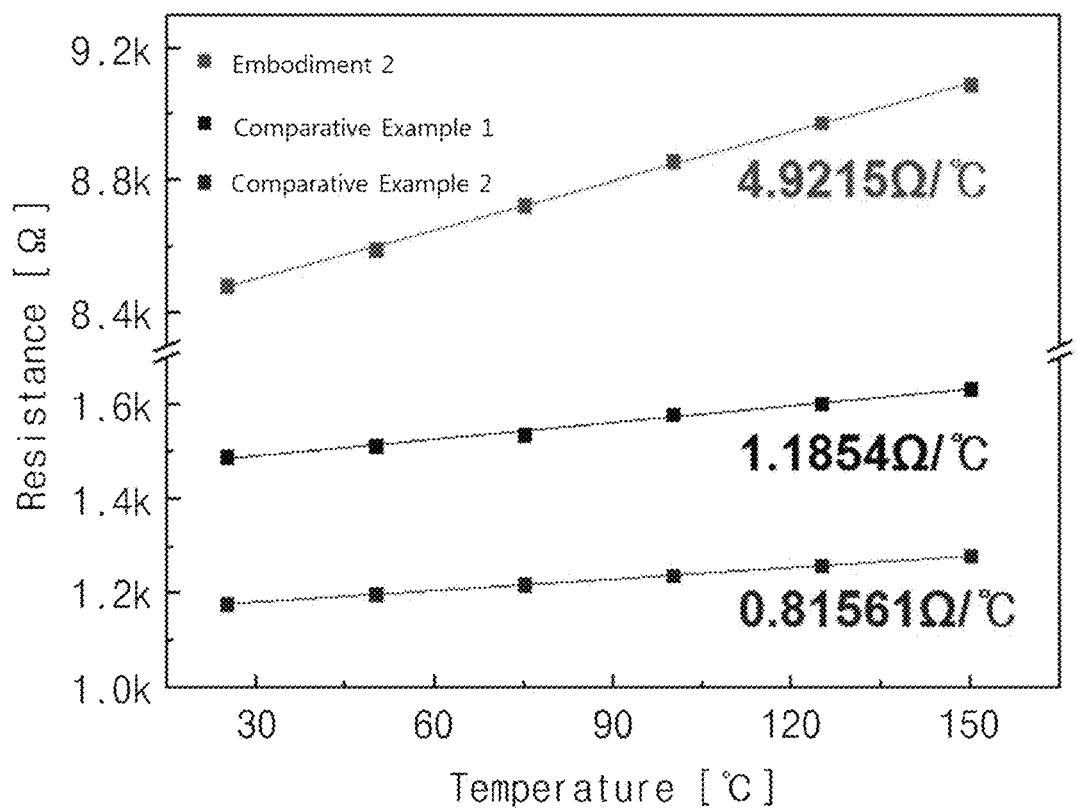

[FIG. 42]
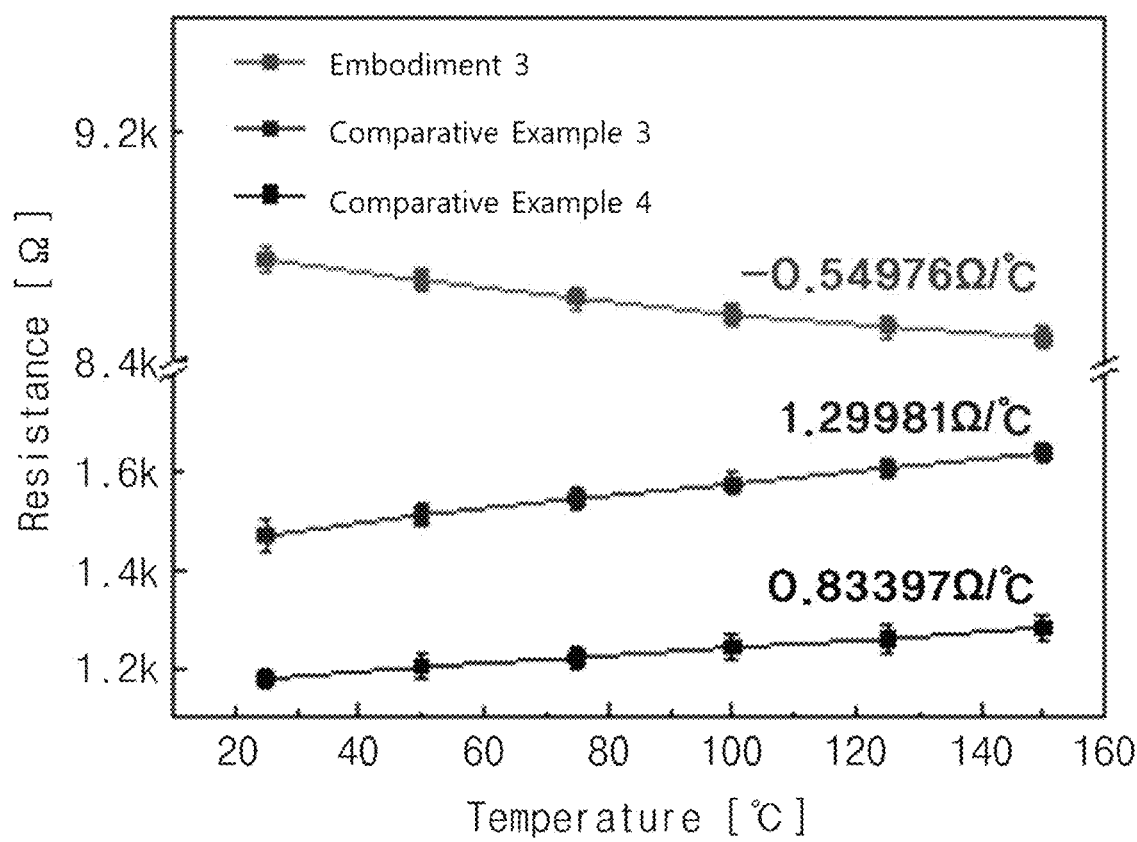

[FIG. 43]
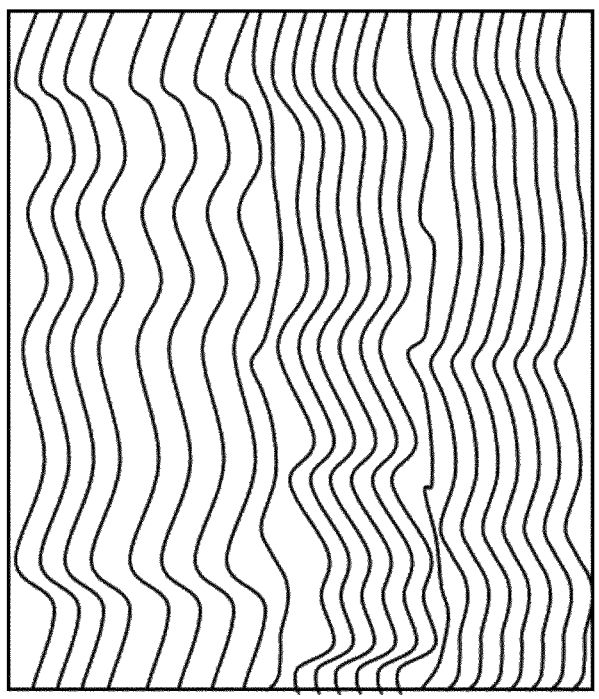

STRETCHABLE MULTIMODAL SENSOR AND METHOD OF FABRICATING OF THE SAME

CROSS-REFERENCE TO RELATED APPLICATION

This U.S. non-provisional patent application claims priority under 35 U.S.C. § 119 to Korean Patent Application No. 10-2017-0119534, filed on Sep. 18, 2017, in the Korean Intellectual Property Office, the disclosure of which is hereby incorporated by reference in its entirety.

BACKGROUND

1. Field

The present disclosure herein relates to a stretchable multimode sensor and a method of fabricating the same, and more particularly, to a stretchable multimode sensor including a pressure sensor, an optical sensor and a thermal sensor which contain amorphous metals, and a method of fabricating the same.

2. Description of the Related Art

As various wearable devices have been developed, various sensors have been used in various fields such as health, health care and education.

A touch sensor which is most usually used is one of pressure sensors and used for a user interface which makes communication between a device and a human. An electronic skin is composed of an electronic components network which can sense these touches, and may be utilized for an interface of an intelligent robot, a biomimetic prosthetic apparatus which are applied to rehabilitation medicine and a remote health robot. As a next generation technology, a flexible touch sensor which is skin attachable and has sensing ability for temperature and pressure gradient, is applicable to a user interface of a mobile device and a wearable device.

A pressure sensor with a conductive layer using a conductive nanotube has been mainly used, however, may be split or cracked by external force because the conductive nanotube does not have flexibility. Accordingly, it is necessary for the wearable devices to reserve electrical characteristics under external mechanical stress. Flexible conductive layers should be formed in the sensor in order to achieve a flexible touch sensor which is usable as the next generation technology.

Thus, researches on a sensor which maintains electrical characteristics under external physical force, has been widely carried out.

SUMMARY

Embodiments of the inventive concepts may provide a stretchable multimode sensor with improved life.

Embodiments of the inventive concepts may also provide a stretchable multimode sensor with improved performance.

Embodiments of the inventive concepts may further provide a method of fabricating a stretchable multimode sensor which is easily produced to have a large area.

Embodiments of the inventive concepts may further provide a method of fabricating a stretchable multimode sensor which is manufactured in a short process time.

Embodiments of the inventive concepts may further provide a method of fabricating a stretchable multimode sensor which is manufactured at a low cost.

In an aspect, a stretchable multimode sensor may include a substrate which is formed of a flexible material and includes a pressure sensor area, an optical sensor area, a temperature sensor area and a switching element area, a pressure sensor which is disposed on the pressure sensor area and includes an amorphous metal, an optical sensor which is disposed on the optical sensor area and includes an amorphous metal, a temperature sensor which is disposed on the temperature sensor area and includes an amorphous metal, and a switching element which is disposed on the switching element area and includes an amorphous metal.

In an embodiment, the pressure sensor may include an elastic layer which is disposed on the pressure sensor area and a lower electrode which is disposed on the elastic layer and includes an amorphous metal.

In an embodiment, the elastic layer may include a convex portion and a concave portion, and the lower electrode may be formed conformally on the elastic layer.

In an embodiment, the pressure sensor may further include an upper electrode facing the lower electrode, and the upper electrode may be formed in planar shape and include an amorphous metal.

In an embodiment, the optical sensor may include an optical sensor gate electrode which is disposed on the optical sensor area and includes an amorphous metal, an optical sensor insulating layer disposed on the optical sensor gate electrode, an optical sensor active layer disposed on the optical sensor insulating layer, and optical sensor source/drain electrodes spaced apart from each other on the optical sensor active layer.

In an embodiment, the temperature sensor may include a pattern electrode which is disposed on the temperature sensor area and includes an amorphous metal and a temperature sensor insulating layer which is disposed on the pattern electrode.

In an embodiment, the pattern electrode may be FeZr/Pt, and the FeZr may be in an amorphous state.

In an embodiment, the switching element may include a switching element gate electrode which is disposed on the switching element area and includes an amorphous metal, a switching element insulating layer which is disposed on the switching element gate electrode, a switching element active layer which is disposed on the switching element insulating layer, and switching element source/drain electrodes spaced apart from each other on the switching element active layer.

In an embodiment, at least one of the pressure sensor, the optical sensor, the temperature sensor or the switching element may include an electrode having a core-shell structure which comprises a core and a shell surrounding the core. The core may be formed of one of an amorphous metal and a crystalline metal, and the shell may be formed of the other of the amorphous metal and the crystalline metal.

In an aspect, a method of fabricating a stretchable multimode sensor may include preparing a substrate which is formed of a flexible material and includes a pressure sensor area, an optical sensor area, a temperature sensor area and a switching element area, and forming a pressure sensor, an optical sensor, a temperature sensor and a switching element on the pressure sensor area, the optical sensor area, the temperature sensor area, the switching element area, respectively. The pressure sensor, the optical sensor, the temperature sensor and the switching element may include the same chemical element which is provided by the same process.

In an embodiment, the pressure sensor, the optical sensor, the temperature sensor and the switching element may further include a crystalline metal which includes the same chemical element provided by the same process and is stacked on the amorphous metal.

In an aspect, a method of fabricating an amorphous thin film may include disposing a source including two or more kinds of metal chemical elements, and a substrate in a chamber, and performing a sputtering process to fabricate an amorphous thin film on the substrate from the source. Flexibility of the amorphous thin film may be controlled by controlling a process pressure in the chamber.

In an embodiment, the process pressure in the chamber may be a minimum pressure which generates plasma in the chamber.

In an embodiment, a length of a void extending from a surface of the amorphous thin film in a depth direction may be controlled depending on the process pressure in the chamber.

In an embodiment, the length of the void may increase as the process pressure in the chamber increases, and the length of the void may decrease as the process pressure in the chamber decreases.

In an embodiment, the flexibility of the amorphous thin film may decrease as the process pressure in the chamber increases, and the flexibility of the amorphous thin film may increase as the process pressure in the chamber decreases.

In an embodiment, the substrate may be a polymer substrate.

In an embodiment, a region in which a polymer of the polymer substrate is mixed with a metal of the amorphous thin film may be provided at an interface between the polymer substrate and the amorphous thin film.

In an embodiment, the polymer substrate may be cooled or quenched after the fabrication of the amorphous thin film, such that a wrinkle structure is generated at the amorphous thin film.

In an embodiment, the amorphous thin film may include an early transition metal and a late transition metal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a flowchart illustrating a method of fabricating a stretchable multimode sensor according to an embodiment of the inventive concepts.

FIGS. 2 to 8 are views illustrating a method of fabricating a stretchable multimode sensor according to an embodiment of the inventive concepts.

FIG. 9 is a structural deformation diagram according to external force of a crystalline metal.

FIG. 10 is a structural deformation diagram according to external force of an amorphous metal.

FIG. 11 shows an optical image of a Ti thin film in a bending situation and a magnified image of a portion of the optical image.

FIG. 12 shows an optical image of a FeZr thin film in a bending situation and a magnified image of a portion of the optical image.

FIG. 13 a graph showing sheet resistances according to a bending diameter of various metal thin films.

FIG. 14 a graph showing sheet resistances according to an elongation of various metal thin films.

FIG. 15 is a schematic diagram showing a Volmer-Weber mode which has a column structure.

FIG. 16 is a schematic diagram showing a Stranski-Krastanov mode with partial voids.

FIG. 17 is a schematic diagram showing a Frank-van der Merwe mode which has a compact amorphous structure.

FIG. 18 is a schematic diagram showing atomic growth with low kinetic energy.

FIG. 19 is a schematic diagram showing atomic growth with intermediate kinetic energy.

FIG. 20 is a schematic diagram showing atomic growth with high kinetic energy.

FIG. 21 is a high-angle annular dark-field scanning transmission electron microscopy (HAADF-STEM) image of a FeZr thin film deposited at a high pressure.

FIG. 22 is a HAADF-STEM image of a FeZr thin film deposited at an intermediate pressure.

FIG. 23 is a HAADF-STEM image of a FeZr thin film deposited at a low pressure.

FIG. 24 shows a transmission electron microscope (TEM) image of FeZr deposited at 3mTorr and an inserted image of fast-Fourier-transform (FFT) data.

FIG. 25 shows energy dispersive X-ray spectroscopy (EDS) data of FeZr deposited at 3mTorr.

FIG. 26 shows a TEM image of FeZr deposited at 11 mTorr and an inserted image of the FFT data.

FIG. 27 shows EDS data of FeZr deposited at 11 mTorr.

FIG. 28 shows a current-voltage graph showing pressure sensing performance when different forces are applied to a pressure sensor including an amorphous metal according to an embodiment of the inventive concepts, and a schematic view of the pressure sensor.

FIG. 29 is a graph showing heart beat rate data measured using a pressure sensor according to an embodiment of the inventive concepts.

FIG. 30 is a graph showing a relative resistance change of a pressure sensor according to an embodiment of the inventive concepts and relative resistance changes of pressure sensors using Ta and Ti.

FIG. 31 is a graph showing repeatability characteristics of a pressure sensor according to an embodiment of the inventive concepts.

FIG. 32 is a graph showing electrical characteristics, under various magnitudes of sounds, of a pressure sensor according to an embodiment of the inventive concepts which is used as a sound detection sensor.

FIG. 33 is a graph showing electrical characteristics, under music, of a pressure sensor according to an embodiment of the inventive concepts which is used as a sound detection sensor.

FIG. 34 is a perspective view illustrating a stretchable multimode sensor according to an embodiment of the inventive concepts.

FIG. 35 is a graph showing temperature sensing performance of a FeZr thin film according to an embodiment of the inventive concepts, an Au thin film, and a Pt thin film.

FIG. 36 is a graph showing heater performance of a FeZr thin film according to an embodiment of the inventive concepts, a Ti thin film, and a Pt thin film.

FIG. 37 is a graph showing electrical characteristics, under light wavelengths, of an In—Zn—O thin film transistor (IZO TFT) including a FeZr electrode according to an embodiment of the inventive concepts.

FIG. 38 is a graph showing electrical characteristics, under elongation stress, of an IZO TFT including a FeZr electrode according to an embodiment of the inventive concepts.

FIG. 39 is a graph illustrating resistance characteristics of an amorphous metal and a crystalline metal in accordance with applied physical force.

FIG. 40 is a voltage-current graph according to a wavelength of an optical sensor in a stretchable multimode sensor according to an embodiment of the inventive concepts.

FIG. 41 is a voltage-resistance graph according to a pattern electrode material and a structure of a temperature sensor included in a stretchable multimode sensor according to an embodiment of the inventive concepts.

FIG. 42 is a voltage-resistance graph according to a pattern electrode material of a temperature sensor included in a stretchable multimode sensor according to an embodiment of the inventive concepts.

FIG. 43 is a view illustrating a wrinkle structure formed at an amorphous thin film according to an embodiment of the inventive concepts.

DETAILED DESCRIPTION OF THE EMBODIMENTS

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

It will be understood that when an element such as a layer, region or substrate is referred to as being "on" another element, it can be directly on the other element or intervening elements may be present. In addition, in the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. As used herein, the term "and/or" includes any and all combinations of one or more of the associated listed items.

The terminology used herein is for the purpose of describing particular embodiments only and is not intended to limit the invention. As used herein, the singular terms "a", "an" and "the" are intended to include the plural forms as well, unless the context clearly indicates otherwise. It will be further understood that the terms "comprises", "comprising", "includes", "including", "have", "has" and/or "having" when used herein, specify the presence of stated features, integers, steps, operations, elements, and/or components, but do not preclude the presence or addition of one or more other features, integers, steps, operations, elements, components, and/or groups thereof. Furthermore, it will be understood that when an element is referred to as being "connected" or "coupled" to another element, it may be directly connected or coupled to the other element or intervening elements may be present.

In addition, in explanation of the present invention, the descriptions to the elements and functions of related arts may be omitted if they obscure the subjects of the inventive concepts.

FIG. 1 is a flowchart illustrating a method of fabricating a stretchable multimode sensor according to an embodiment of the inventive concepts, and FIGS. 2 to 8 are views illustrating a method of fabricating a stretchable multimode sensor according to an embodiment of the inventive concepts.

Referring to FIGS. 1 and 2, a substrate 100 may be prepared (S110). The substrate may be formed of a flexible material and include a pressure sensor area 110, an optical sensor area 120, a temperature sensor area 130 and a switching element area 140.

The substrate 100 may be formed of a flexible material. In some embodiments, the substrate 100 may be formed of a paper. In other embodiments, the substrate 100 may be formed of polyethylene terephthalate (PET), polyimide (PI), polycarbonate (PC), nano-cellulose (NC) or rubber to have heat resistance and chemical resistance.

In some embodiments, the substrate 100 may include the pressure sensor area 110, the optical sensor area 120 and the temperature sensor area 130 and include a plurality of switching element areas 140 which correspond to the pressure sensor area 110, the optical sensor area 120 and the temperature sensor area 130, respectively. Specifically, the substrate 100 may include the pressure sensor area 110 and the switching element area 140 corresponding thereto, the optical sensor area 120 and the switching element area 140 corresponding thereto, and the temperature sensor area 130 and the switching element area 140 corresponding thereto. The switching element areas 140 may be located adjacent to the pressure sensor area 110, the optical sensor area 120 and the temperature sensor area 130, respectively.

In other embodiments, the substrate 100 may include the pressure sensor area 110, the optical sensor area 120 and the temperature sensor area 130 and include a plurality of switching element areas 140 which corresponds to the pressure sensor area 110, the optical sensor area 120 and the temperature sensor area 130, respectively. The switching element areas 140 may be provided in the pressure sensor area 110, the optical sensor area 120 and the temperature sensor area 130, respectively.

Referring to FIGS. 1 and 3 to 8, a pressure sensor 200, an optical sensor 300, a temperature sensor 400 and a switching element 500 may be formed on the pressure sensor area 110, the optical sensor area 120, the temperature sensor area 130 and the switching element area 140, respectively (S120).

The pressure sensor 200, the optical sensor 300, the temperature sensor 400 and the switching element 500 may be formed to include an amorphous metal.

Referring to FIG. 3, an elastic layer 210 may be formed on the pressure sensor area 110 of the substrate 100.

The elastic layer 210 may be provided in various shaped structures. In some embodiments, the elastic layer 210 may be provided in a planar structure. In other embodiments, the elastic layer 210 may have a convex portion and a concave portion.

In some embodiments, the elastic layer 210 may include at least one of PDMS, poly-urethane acrylate (PUA) or Ecoflex. In some embodiments, the elastic layer 210 may be formed of the same material as the substrate 100.

In some embodiments, the elastic layer 210 may be formed using a silicone mold.

Referring to FIG. 4, a lower electrode 220 may be formed on the elastic layer 210 of the pressure sensor area 110, an optical sensor gate electrode 310 may be formed on the optical sensor layer 120, a pattern electrode 410 may be formed on the temperature sensor area 130, and a switching element gate electrode 510 may be formed on the switching element area 140. In some embodiments, thicknesses of the lower electrode 220, the optical sensor gate electrode 310, the pattern electrode 410 and the switching element gate electrode 510 may be 1 nm or more.

The lower electrode 220, the optical sensor gate electrode 310, the pattern electrode 410 and the switching element gate electrode 510 may include the amorphous metal having the same chemical element which is provided by the same process.

In some embodiments, the lower electrode 220, the optical sensor gate electrode 310, the pattern electrode 410 and the switching element gate electrode 510 may be formed at the same time by the same process using an amorphous metal of the same chemical element.

In other embodiments, the lower electrode 220, the optical sensor gate electrode 310, the pattern electrode 410 and the switching element gate electrode 510 may be formed at the same time by the same process using an amorphous metal of the same chemical element and a crystalline metal of the same chemical element.

In an embodiment, the lower electrode 220, the optical sensor gate electrode 310, the pattern electrode 410 and the switching element gate electrode 510 may have a structure in which one of the amorphous metal and the crystalline metal is formed on the other of the amorphous metal and the crystalline metal.

In another embodiment, the lower electrode 220, the optical sensor gate electrode 310, the pattern electrode 410 and the switching element gate electrode 510 may be formed in a nano-laminate structure in which amorphous metal layers and crystalline metal layers are alternately stacked.

In still another embodiment, the lower electrode 220, the optical sensor gate electrode 310, the pattern electrode 410 and the switching element gate electrode 510 may be formed in a core-shell structure which includes a core and a shell surrounding the core. Specifically, a lower shell may be formed on the elastic layer 210 of the pressure sensor area 110, the optical sensor area 120, the temperature sensor area 130, and the switching element area 140. The core which is narrower than the lower shell may be formed on the lower shell, and an upper shell with the same width as the lower shell may be formed on the core. In some embodiments, the core and the shell may be formed by a sputtering technique, an E-beam evaporating technique, an ink jet printing technique, a screen printing technique, a spraying technique, a brush painting technique, a doctor blade technique, or a spin coating technique.

The core may be formed of one of the amorphous metal and the crystalline metal, and the shell may be formed of the other of the amorphous metal and the crystalline metal.

In some embodiments, the lower electrode 220, the optical sensor gate electrode 310, the pattern electrode 410 and the switching element gate electrode 510 may be formed by a sputtering technique, an E-beam evaporating technique, an ink jet printing technique, a screen printing technique, a spraying technique, a brush painting technique, a doctor blade technique, or a spin coating technique.

In some embodiments, the lower electrode 220, the optical sensor gate electrode 310, the pattern electrode 410 and the switching element gate electrode 510 may include at least one of FeZr, CoTi, CoNi, NiTi, Fe—Nb—Al composite, La—Al—Cu, Al—Sc, ZrTiCuNiBe, AuSi, TiCoPdZr, or MgZnCa. In an embodiment, the pattern electrode 410 may include FeZr/Pt, and FeZr may be in an amorphous state.

In other embodiments, the lower electrode 220 may include at least one of $BaTiO_3$ or $PbZrTiO_3$.

In some embodiments, the lower electrode 220 may be formed conformally on the elastic layer 210.

Referring to FIG. 5, an optical sensor insulating layer 320 may be formed on the optical sensor gate electrode 310 of the optical sensor area 120, a temperature sensor insulating layer 420 may be formed on the pattern electrode 410 of the temperature sensor area 130, and a switching element insulating layer 520 may be formed on the switching element gate electrode 510 of the switching element area 140.

The optical sensor insulating layer 320, the temperature sensor insulating layer 420 and the switching element insulating layer 520 may be formed simultaneously using the same material.

In some embodiments, the optical sensor insulating layer 320, the temperature sensor insulating layer 420 and the switching element insulating layer 520 may be formed by a sputtering technique, an E-beam evaporating technique, an ink jet printing technique, a screen printing technique, a spraying technique, a brush painting technique, a doctor blade technique, or a spin coating technique.

In some embodiments, the optical sensor insulating layer 320, the temperature sensor insulating layer 420 and the switching element insulating layer 520 may include at least one of $SiO_2$, SiON, $Si_3N_4$, or a metal oxide.

Referring to FIG. 6, an optical sensor active layer 330 may be formed on the optical sensor insulating layer 320 of the optical sensor area 120, and a switching element active layer 530 may be formed on the switching element insulating layer 520 of the switching element area 140.

In some embodiments, the optical sensor active layer 330 and the switching element active layer 530 may be formed simultaneously using the same material.

In certain embodiments, the optical sensor active layer 330 and the switching element active layer 530 may be formed sequentially using different materials.

In some embodiments, the optical sensor active layer 330 may include a photosensitive semiconductor such as indium zinc oxide (IZO), zinc oxide (ZnO), $MoS_2$, $MoSe_2$, $WS_2$, $WSe_2$, or titanium oxide (TiO).

In some embodiments, the switching element active layer 530 may include indium gallium zinc oxide (IGZO), indium zinc oxide (IZO), zinc oxide (ZnO), $MoS_2$, $MoSe_2$, $WS_2$, $WSe_2$, or titanium oxide (TiO).

In some embodiments, the optical sensor active layer 330 and the switching element active layer 530 may be formed by a sputtering technique, an E-beam evaporating technique, an ink jet printing technique, a screen printing technique, a spraying technique, a brush painting technique, a doctor blade technique, or a spin coating technique.

Referring to FIG. 7, optical sensor source/drain electrodes 340 may be formed on the optical sensor active layer 330 of the optical sensor area 120, and switching element source/drain electrodes 540 may be formed on the switching element active layer 530 of the switching element area 140. In some embodiments, the optical sensor source/drain electrodes 340 and the switching element source/drain electrodes 540 may have thicknesses of 1 nm or more.

The optical sensor source/drain electrodes 340 and the switching element source/drain electrodes 540 may include an amorphous metal of the same chemical element which is provided by the same process.

In some embodiments, the optical sensor source/drain electrodes 340 and the switching element source/drain electrodes 540 may be formed simultaneously by the same process using the amorphous metal of the same chemical element.

In certain embodiments, the optical sensor source/drain electrodes 340 and the switching element source/drain electrodes 540 may be formed simultaneously by the same process using the amorphous metal of the same chemical element and a crystalline metal of the same chemical element.

In an embodiment, the optical sensor source/drain electrodes 340 and the switching element source/drain electrodes 540 may have a structure in which one of the amorphous metal and the crystalline metal is formed on the other of the amorphous metal and the crystalline metal.

In another embodiment, the optical sensor source/drain electrodes 340 and the switching element source/drain electrodes 540 may be formed in a nano-laminate structure in which amorphous metal layers and crystalline metal layers are alternately stacked.

In still another embodiment, the optical sensor source/drain electrodes 340 and the switching element source/drain electrodes 540 may be formed in a core-shell structure which includes a core and a shell surrounding the core. The core may be formed of one of the amorphous metal and the crystalline metal, and the shell may be formed of the other of the amorphous metal and the crystalline metal.

In some embodiments, the optical sensor source/drain electrodes 340 and the switching element source/drain electrodes 540 may be formed by a sputtering technique, an E-beam evaporating technique, an ink jet printing technique, a screen printing technique, a brush painting technique, a doctor blade technique, or a spin coating technique.

In some embodiments, the optical sensor source/drain electrodes 340 and the switching element source/drain electrodes 540 may include at least one of FeZr, CoTi, CoNi, NiTi, Fe—Nb—Al composite, La—Al—Cu, Al—Sc, ZrTi-CuNiBe, AuSi, TiCoPdZr, or MgZnCa.

Referring to FIG. 8, a pressure sensor 200, an optical sensor 300, a temperature sensor 400 and a switching element 500 may be fabricated.

The pressure sensor 200 may further include an upper electrode 240 which faces the lower electrode 220. Specifically, the pressure sensor 200 may further include an upper electrode elastic layer 230 which is opposite to the lower electrode 220, and the upper electrode 240 which is disposed on the upper electrode elastic layer 230 and faces the lower electrode 220.

In some embodiments, the upper electrode elastic layer 230 may be formed of the same material as the elastic layer 210 and may be provided in a planar structure.

In some embodiments, the upper electrode 240 may be provided in planar structure and include an amorphous metal. In some embodiments, the upper electrode 240 may be formed of the same material as the lower electrode 220. In some embodiments, the upper electrode 240 may be formed conformally on the upper electrode elastic layer 230.

Unlike the embodiments of the inventive concepts, if the pressure sensor 200, the optical sensor 300, the temperature sensor 400 and the switching element 500 do not include the amorphous metal, elasticity of the amorphous metal may not be provided, and thus life span of a stretchable sensor may be reduced and characteristics of a stretchable sensor may be deteriorated.

However, according to the embodiments of the inventive concepts, the pressure sensor 200, the optical sensor 300, the temperature sensor 400 and the switching element 500 may include the amorphous metal, and thus life span of the stretchable multimode sensor may be increased and characteristics of the stretchable multimode sensor may be improved.

In addition, when the pressure sensor 200, the optical sensor 300, the temperature sensor 400 and the switching element 500 include the amorphous metal as the embodiments of the inventive concepts, the stretchable multimode sensor having excellent flexibility and elasticity may be provided by properties of the amorphous metal having irregular atom arrangement.

Furthermore, according to the embodiments of the inventive concepts, the pressure sensor 200, the optical sensor 300, the temperature sensor 400 and the switching element 500 may include the amorphous metal which is formed by the same process using the same chemical element. Thus, it is possible to provide the method of fabricating the stretchable multimode sensor which is capable of reducing a process time and a process cost.

According to some embodiments of the inventive concepts, an elongation of an amorphous thin film may be controlled depending on a process pressure in a sputtering process. In detail, when the process pressure is relatively high, a void which is longish in a depth direction may be generated at a surface of the amorphous thin film. When the process pressure is relatively low, the amorphous thin film may not include a void or may have a short void, and thus the amorphous thin film may have high flexibility. In other words, the long void may act as a notch by physical deformation and thus may reduce the flexibility of the amorphous thin film. Thus, when high flexibility is required, the sputtering process may be performed at a minimum pressure condition capable of generating plasma in a chamber in which the sputtering process is performed, thereby maximizing the flexibility of the amorphous thin film.

In addition, a growth rate of the amorphous thin film may be relatively high when the process pressure is relatively high, and the growth rate of the amorphous thin film may be relatively low when the process pressure is relatively low. Thus, when a portion requiring flexibility is formed, the flexibility may be secured by reducing the process pressure. When a portion not requiring flexibility is formed, the growth or deposition rate of the amorphous thin film may be increased by increasing the process pressure. In addition, when a device broken by physical deformation (not a device of which reliability is slightly changed by flexibility) is required, the flexibility of the amorphous thin film may be reduced by increasing the process pressure. As a result, the process pressure may be controlled depending on application of the amorphous thin film according to the embodiments of the inventive concepts, and thus the flexibility and deposition rate of the amorphous thin film may be controlled.

Moreover, when a sputtering process is performed on a polymer substrate (e.g., a PDMS substrate) to form the amorphous thin film, a top surface of the polymer substrate may be partially melted to be mixed with metal particles in an initial stage in which metal particles having high energy are deposited on the polymer substrate. Thereafter, when the melted portion is cooled or quenched, the polymer substrate may be contracted to form a wrinkle structure at the amorphous thin film, as illustrated in FIG. 43. The flexibility of the amorphous thin film may be improved by the wrinkle structure of the amorphous thin film. The wrinkle structure may be generated by a material having a low surface tension, e.g., a metal (e.g., FeZr) which is easily wettable with a polymer.

Furthermore, the amorphous thin film according to an embodiment of the inventive concepts may be formed by depositing metal chemical elements having different sizes at the same time. For example, an early transition metal and a late transition metal may be deposited at the same time to easily form the amorphous thin film. In this case, a metal chemical element having a different size may be additionally provided.

Hereinafter, detailed experimental examples of a stretchable multimode sensor according to embodiments of the inventive concepts will be described.

FIG. 9 is a structural deformation diagram according to external force of a crystalline metal, and FIG. 10 is a structural deformation diagram according to external force of an amorphous metal.

Referring to FIG. 9, when external force is applied to a crystalline metal, a slip plane of a lattice of the crystalline metal is broken to form a discontinuous portion. On the contrary, referring to FIG. 10, since an amorphous metal does not have a lattice structure, atomic deformation of the amorphous metal occurs but the amorphous metal is not easily broken.

As a result, it may be recognized that the amorphous metal is suitable for use in the stretchable multimode sensor according to some embodiments of the inventive concepts. In detail, it may be recognized that the amorphous metal is suitable for use in the pressure sensor, the optical sensor, the temperature sensor and the switching element of the stretchable multimode sensor.

According to some embodiments of the inventive concepts, an amorphous FeZr thin film and a crystalline Ti thin film may be comparatively analyzed to evaluate mechanical properties of the amorphous metal.

FIG. 11 shows an optical image of a Ti thin film in a bending situation and a magnified image of a portion of the optical image, and FIG. 12 shows an optical image of a FeZr thin film in a bending situation and a magnified image of a portion of the optical image.

Referring to FIGS. 11 and 12, the crystalline Ti thin film has a lattice structure, unlike the amorphous FeZr thin film. Thus, when external stress is applied to the Ti thin film, a crack may occur at the Ti thin film. A resistance of the Ti thin film may be increased by the crack, and thus it may be difficult to use the Ti thin film as an electrode. On the contrary, a crack is not observed in the FeZr thin film after a bending situation.

As a result, it may be recognized that the amorphous FeZr thin film is suitable for use in the stretchable multimode sensor according to some embodiments of the inventive concepts.

FIG. 13 a graph showing sheet resistances according to a bending diameter of various metal thin films, and FIG. 14 a graph showing sheet resistances according to an elongation of various metal thin films.

Referring to FIG. 13, in a folding situation, a Ti thin film has the greatest resistance, and the FeZr thin film has the smallest resistance. Resistances of a Ta thin film and a Cu thin film are between the resistance of the Ti thin film and the resistance of the FeZr thin film, and the resistance of the Ta thin film is greater than the resistance of the Cu thin film. Referring to FIG. 14, when external stress is applied, the Ti thin film has the greatest resistance, the FeZr thin film has the smallest resistance, and resistances of the Ta thin film and the Cu thin film are between the resistance of the Ti thin film and the resistance of the FeZr thin film. The resistance of the Ta thin film is greater than the resistance of the Cu thin film.

As a result, mechanical properties of the FeZr thin film are excellent as compared with those of the Ti thin film, the Ta thin film and the Cu thin film. Thus, it may be recognized that the FeZr thin film is suitable for use in the stretchable multimode sensor according to some embodiments of the inventive concepts.

According to some embodiments of the inventive concepts, amorphous metal films having different growth modes may be analyzed to verify control of porosity of an amorphous metal thin film.

FIG. 15 is a schematic diagram showing a Volmer-Weber mode which has a column structure, FIG. 16 is a schematic diagram showing a Stranski-Krastanov mode with partial voids, and FIG. 17 is a schematic diagram showing a Frank-van der Merwe mode which has a compact amorphous structure.

Referring to FIG. 15, Fe and Zr atoms may interact with argon atoms at high pressures, and thus mean-free paths of Fe and Zr atoms may be shortened. In addition, at high pressures, the mobility of atoms at a surface of a growing film may be reduced, and thus a void structure due to a shadowing effect may be formed. Since the mobility of the atoms is reduced as described above, the atoms may interact with each other due to low kinetic energy, and atomic clusters may be formed. Finally, a columned structure with randomly located voids may be formed according to the Volmer-Weber mode.

On the contrary, referring to FIG. 16, dense FeZr may be formed on a surface of a substrate at intermediate pressures. However, the dense FeZr may gradually grow with a columned structure in the Stranski-Krastanov mode.

Referring to FIG. 17, mean-free paths of the atoms may be increased due to high kinetic energy of the atoms deposited at a low pressure, and thus a compact amorphous structure may be formed. In this case, the amount of interaction between the deposited atoms with argon may be decreased to form a smooth surface of a thin film.

In addition, sputtered atoms may be adsorbed on the surface of the thin film, and thus it is possible to prevent the sputtered atoms from diffusing to form an equilibrium lattice. Each element may effectively suppress the atomic mobility of other atoms, and thus the atoms may be easily deposited into an amorphous structure with an alloy metal. In this case, the amorphous film may be uniformly formed without voids or grain boundaries in the Frank-van der Merwe mode.

FIG. 18 is a schematic diagram showing atomic growth with low kinetic energy, FIG. 19 is a schematic diagram showing atomic growth with intermediate kinetic energy, and FIG. 20 is a schematic diagram showing atomic growth with high kinetic energy.

Referring to FIGS. 18 to 20, a growth structure of atoms in a thin film depends on the deposition pressure.

According to some embodiments of the inventive concepts, to check a structure of an amorphous metal thin film structure considering kinetic energy of sputtered atoms, FeZr thin films having thicknesses of 50 nm may be deposited at different pressures of 3 mTorr, 7 mTorr, and 11 mTorr. Thus, structures of the FeZr thin films deposited at the different pressures may be analyzed and void structures in the thin films may be adjusted.

FIG. 21 is a high-angle annular dark-field scanning transmission electron microscopy (HAADF-STEM) image of a FeZr thin film deposited at a high pressure, FIG. 22 is a HAADF-STEM image of a FeZr thin film deposited at an intermediate pressure, and FIG. 23 is a HAADF-STEM image of a FeZr thin film deposited at a low pressure.

Referring to FIG. 21, a FeZr thin film deposited at a high pressure has a void structure between columns. Referring to FIG. 22, a FeZr thin film deposited at an intermediate pressure has a mixture of compact and void structures. On the contrary, referring to FIG. 23, a FeZr thin film deposited at a low pressure has a compact amorphous structure, unlike the FeZr thin films deposited at the high pressure and the intermediate pressure.

FIG. 24 shows a transmission electron microscope (TEM) image of FeZr deposited at 3 mTorr and an inserted image of fast-Fourier-transform (FFT) data, and FIG. 25 shows energy dispersive X-ray spectroscopy (EDS) data of FeZr deposited at 3 mTorr. FIG. 26 shows a TEM image of FeZr deposited at 11 mTorr and an inserted image of the FFT data, and FIG. 27 shows EDS data of FeZr deposited at 11 mTorr.

Referring to FIGS. 24 and 25, FeZr which is an amorphous metal may be deposited on a substrate with high energy during sputtering when a deposition pressure is low. Thus, FeZr may form a complete amorphous structure.

On the contrary, referring to FIGS. 26 and 27, porous voids are formed at an interface between a surface of FeZr and a substrate when the deposition pressure is high.

FIG. 28 shows a current-voltage graph showing pressure sensing performance when different forces are applied to a pressure sensor including an amorphous metal according to an embodiment of the inventive concepts, and a schematic view of the pressure sensor.

Referring to FIG. 28, the pressure sensor shows the pressure sensing performance in a range of 100 Pa to 5 kPa. Since linear curves are shown in the current-voltage graph, ohmic behavior with different loading pressures may be confirmed. In addition, a resistance value increases as the loading pressure increases.

FIG. 29 is a graph showing heart beat rate data measured using a pressure sensor according to an embodiment of the inventive concepts.

Referring to FIG. 29, it may be recognized that a heart rate is easily measured using the pressure sensor attached on the skin. Typically, a health condition of a user may be checked using the blood flow amplitude $P_1$ and reflected waves ($P_2$: wrist, $P_3$: lower body) due to the contraction of the heart muscle. For example, a radial artery elevation index (AIr=$P_2$/ $P_1$), radial diastolic augmentation (DAI=$P_3$/ $P_1$), and the travel time of waves reflected from the hand ($T_R$) may be commonly used for a quantitative evaluation of atherosclerosis.

FeZr may be more conductive than typical conductive polymers and may be operated at extremely low voltages (~1 mV). These high-performance and low-power-consumption characteristics may be suitable for wearable devices with limited power capacities.

FIG. 30 is a graph showing a relative resistance change of a pressure sensor according to an embodiment of the inventive concepts and relative resistance changes of pressure sensors using Ta and Ti, and FIG. 31 is a graph showing repeatability characteristics of a pressure sensor according to an embodiment of the inventive concepts.

Referring to FIG. 30, the durability (~$10^5$) of the pressure sensor according to the embodiments of the inventive concepts is higher than those of pressure sensors fabricated using crystalline metals such as Ta and Ti.

Referring to FIG. 31, electrical characteristics of the pressure sensor according to the embodiments of the inventive concepts are not changed for 100,000 cycles at 1 kPa. Thus, it may be recognized that the pressure sensor according to the embodiments of the inventive concepts is stably used for a long time.

FIG. 32 is a graph showing electrical characteristics, under various magnitudes of sounds, of a pressure sensor according to an embodiment of the inventive concepts which is used as a sound detection sensor, and FIG. 33 is a graph showing electrical characteristics, under music, of a pressure sensor according to an embodiment of the inventive concepts which is used as a sound detection sensor.

Referring to FIGS. 32 and 33, the pressure sensor may be used as a sound detection sensor sensing various magnitudes of sounds and music and may be applied to various applications.

FIG. 34 is a perspective view illustrating a stretchable multimode sensor according to an embodiment of the inventive concepts.

Referring to FIG. 34, a view (A) of FIG. 34 illustrates a stretchable multimode sensor array 20 which includes a plurality of stretchable multimode sensors 10, and a view (B) of FIG. 34 illustrates a single pixel stretchable multimode sensor 10.

The stretchable multimode sensor 10 may include the pressure sensor 200, the optical sensor 300, the temperature sensor 400, and the switching element 500. In some embodiments, the stretchable multimode sensor 10 may include a plurality of the switching elements 500 corresponding to the pressure sensor 200, the optical sensor 300, the temperature sensor 400, and the switching element 500, respectively. The plurality of switching elements 500 may address the pressure sensor 200, the optical sensor 300, and the temperature sensor 400.

The stretchable multimode sensor 10 and the stretchable multimode sensor array 20 may further include interconnection lines 12.

The interconnection lines 12 may connect the pressure sensor 200, the optical sensor 300, the temperature sensor 400, the switching element 500, and/or the plurality of stretchable multimode sensors 10. In some embodiments, the interconnection lines 12 may have thicknesses of 1 nm or more.

In some embodiments, the interconnection line 12 may include an amorphous metal. In other embodiments, the interconnection line 12 may include an amorphous metal and a crystalline metal. In an embodiment, the interconnection line 12 may have a structure in which one of the amorphous metal and the crystalline metal is formed on the other of the amorphous metal and the crystalline metal. In another embodiment, the interconnection line 12 may be formed in a nano-laminate structure in which amorphous metal layers and crystalline metal layers are alternately stacked. In still another embodiment, the interconnection line 12 may be formed in a core-shell structure which includes a core and a shell surrounding the core. The core may be formed of one of the amorphous metal and the crystalline metal, and the shell may be formed of the other of the amorphous metal and the crystalline metal.

In some embodiments, the interconnection lines 12 may be formed by a sputtering technique, an E-beam evaporating technique, an ink jet printing technique, a screen printing technique, a spraying technique, or a spin coating technique.

In some embodiments, the interconnection lines 12 may include at least one of FeZr, CoTi, CoNi, NiTi, Fe—Nb—Al composite, La—Al—Cu, Al—Sc, ZrTiCuNiBe, AuSi, TiCoPdZr, or MgZnCa.

FIG. 35 is a graph showing temperature sensing performance of a FeZr thin film according to an embodiment of the inventive concepts, an Au thin film, and a Pt thin film.

Referring to FIG. 35, crystalline Au and Pt thin films exhibit positive temperature coefficients on resistance (TCR), and resistances of the Au and Pt thin films increase as a temperature increases. On the contrary, since the amorphous FeZr thin film does not have a lattice structure, an initial resistance of the amorphous FeZr thin film is higher than those of the crystalline Au and Pt thin films. However, the FeZr thin film exhibits a negative TCR, and the resistance of the FeZr thin film decreases as a temperature increases. This phenomenon may be repeatable unless the amorphous structure of the FeZr thin film is ordered in a lattice structure at temperatures above 500° C.

As shown in the graph, the TCR value (5.30405Ω/° C.) of the FeZr thin film is most sensitive in comparison with the Au thin film (1.1854Ω/° C.) and the Pt thin film (0.81561Ω/° C.). In addition, a linear curve is shown in a dynamic range of 25° C. to 150° C.

As a result, the FeZr thin film may be easily used as a temperature sensor.

According to some embodiments of the inventive concepts, to measure an accurate temperature, a heater or a capsule may be produced. The heater may inject drugs into humans through the skin in the form of a micro-needle, and the capsule may react at a certain temperature.

FIG. 36 is a graph showing heater performance of a FeZr thin film according to an embodiment of the inventive concepts, a Ti thin film, and a Pt thin film.

Referring to FIG. 36, a FeZr thin film was deposited on PET and a voltage of 10V was applied to check performance of the FeZr thin film as the heater. As shown in FIG. 36, temperature was measured over time. As a result, the temperature was raised and then became saturated at 80° C. Thus, the FeZr thin film may be easily used as the heater.

FIG. 37 is a graph showing electrical characteristics, under light wavelengths, of an In—Zn—O thin film transistor (IZO TFT) including a FeZr electrode according to an embodiment of the inventive concepts.

Referring to FIG. 37, the transfer characteristics of the photosensor with a channel width and a length of 100 μm and 50 μm are shown. The dependence of the photo-TFT was measured under light wavelengths of 550, 500, 450 and 400 nm and at a power of 200 μWcm$^{-2}$. As shown in the graph of FIG. 37, the IZO TFT including the FeZr electrode is sensitive to specific wavelengths.

FIG. 38 is a graph showing electrical characteristics, under elongation stress, of an IZO TFT including a FeZr electrode according to an embodiment of the inventive concepts.

Referring to FIG. 38, the IZO TFT retains a certain level of electrical characteristics with an on current of 1.4 μA when the FeZr electrode was stretched 15%. A typical stretchable device may present operating characteristics below 10%. Thus, the FeZr electrode may be used as a core material in stretchable electronics created using typical semiconductorfabrication processes.

FIG. 39 is a graph illustrating resistance characteristics of an amorphous metal and a crystalline metal in accordance with applied physical force.

Referring to FIG. 39, it was shown that resistance was changed by elongation percentage of an element including an amorphous metal or a crystalline metal.

An element according to an embodiment 1 has a structure in which an amorphous metal FeZr and a crystalline metal Pt are stacked on a PDMS substrate, an element of an embodiment 2 has a structure in which crystalline metals Ta and Pt are stacked on a PDMS substrate, and an element of an embodiment 3 has a structure in which crystalline metals Ti and Pt are stacked on a PDMS substrate.

The element of the embodiment 1 does not show an outstanding resistance change even if the elongation percentage is increased by external physical force. In contrast, the elements of the embodiments 2 and 3 show outstanding resistance changes as the elongation percentage is increased by external physical force.

Thus, the element including the amorphous metal is suitable to be used as a stretchable sensor because the resistance change caused by external physical force is not outstanding.

FIG. 40 is a voltage-current graph according to a wavelength of an optical sensor included in a stretchable multimode sensor according to an embodiment of the inventive concepts.

Referring to FIG. 40, a voltage-current change was shown according to a wavelength of the optical sensor including the amorphous metal.

Fabrication of Optical Sensor According to Embodiment 1

An optical sensor gate electrode including an amorphous metal FeZr was formed on a substrate, and an optical sensor insulating layer was formed on the optical sensor gate electrode. An optical sensor active layer was formed on the optical sensor insulating layer, and optical sensor source/drain electrodes including an amorphous metal FeZr were formed on the optical sensor active layer. Thus, the optical sensor according to the embodiment 1 was fabricated.

Using the optical sensor according to the embodiment 1, a voltage-current change by a wavelength was measured in a wavelength range of 400 nm to 800 nm.

As the result, the optical sensor was operated without trouble even if the optical sensor included the amorphous metals as the optical sensor gate electrode and the optical sensor source/drain electrode.

FIG. 41 is a voltage-resistance graph according to a pattern electrode material and a structure of a temperature sensor included in a stretchable multimode sensor according to an embodiment of the inventive concepts.

Referring to FIG. 41, a temperature-resistance change of the temperature sensor was shown according to the material and the structure of the pattern electrode.

Fabrication of Temperature Sensor According to Embodiment 2

An amorphous metal FeZr and a crystalline metal Pt were staked on a substrate to form a pattern electrode, and a temperature sensor insulating layer was formed on the pattern electrode to fabricate the temperature sensor according to the embodiment 2.

Fabrication of Temperature Sensors According to Comparative Examples 1 and 2

Crystalline metals Ti and Au were staked on a substrate to form a pattern electrode, and a temperature sensor insulating layer was formed on the pattern electrode to fabricate a temperature sensor according to the comparative example 1.

A pattern electrode was formed using a crystalline metal Pt on a substrate, and a temperature sensor insulating layer was formed on the pattern electrode to fabricate a temperature sensor according to the comparative example 2.

The temperature sensors according to the embodiment 2 and the comparative examples 1 and 2 may be classified as the following table 1.

TABLE 1

|  | Embodiment 2 | Comparative example 1 | Comparative example 2 |
|---|---|---|---|
| Pattern Electrode Material | FeZr/Pt | Ti/Au | Pt |
| Pattern Electrode Structure | Stack | Stack | Single layer |

Using the temperature sensors according to the embodiment 2 and the comparative examples 1 and 2, resistance changes were measured as gradually increasing a temperature in a temperature range of 30° C. to 150° C.

The resistance of the temperature sensor according to the embodiment 2 was significantly increased as increasing the temperature, and Rs was measured as 4.9215Ω/° C. The resistances of the temperature sensors according to the comparative examples 1 and 2 were slightly increased as increasing the temperature, Rs of the temperature sensor according to the comparative example 1 was measured as 1.1854Ω/° C., and Rs of the temperature sensor according to the comparative example 2 was measured as 0.81561Ω/° C.

As a result, the resistance change as increasing temperature was large when the pattern electrode of the temperature sensor had a nano-laminate structure in which different species materials were stacked, as compared with a structure of a single material. In addition, the resistance change as increasing temperature was large when the pattern electrode of the temperature sensor had a nano-laminate structure in which an amorphous metal and a crystalline metal were stacked, as compared with a nano-laminate structure in which different kinds of crystalline metals were stacked.

Thus, it is possible to provide the temperature sensor which has improved sensing ability when the pattern electrode of the temperature sensor has the nano-laminate structure in which the amorphous metal and the crystalline metal are stacked.

FIG. 42 is a voltage-resistance graph according to a pattern electrode material of a temperature sensor included in a stretchable multimode sensor according to an embodiment of the inventive concepts.

Referring to FIG. 42, a temperature-resistance change of the temperature sensor was shown according to the material of the pattern electrode.

Fabrication of Temperature Sensor According to Embodiment 3

A pattern electrode was formed using an amorphous metal FeZr on a substrate, and a temperature sensor insulating layer was formed on the pattern electrode to fabricate a temperature sensor according to the embodiment 3.

Fabrication of Temperature Sensor According to Comparative Examples 3 and 4

A pattern electrode was formed using a crystalline metal Au on a substrate, and a temperature sensor insulating layer was formed on the pattern electrode to fabricate a temperature sensor according to the comparative embodiment 3.

A pattern electrode was formed using a crystalline metal PT on a substrate, and a temperature sensor insulating layer was formed on the pattern electrode to fabricate a temperature sensor according to the comparative embodiment 4, The temperature sensors according to the embodiment 3 and the comparative examples 3 and 4 may be classified as the following table 2.

TABLE 2

|  | Embodiment 3 | Comparative example 3 | Comparative example 4 |
|---|---|---|---|
| Pattern electrode material | FeZr | Au | Pt |

Using the temperature sensor according to the embodiment 3 and the comparative examples 3 and 4, a resistance change was measured as gradually increasing a temperature in a temperature range of about 20° C. to about 150° C.

The resistance of the temperature sensor according to the embodiment 3 was decreased as increasing the temperature, and Rs was measured as −0.54976Ω/° C. The resistances of temperature sensors according to the comparative examples 3 and 4 were slightly increased as increasing the temperature, Rs of the temperature sensor according to the comparative example 3 was measured as 1.29981Ω/° C., and Rs of the temperature sensor according to the comparative example 4 was measured as 0.83397Ω/° C.

According to the embodiments of the inventive concepts, the pressure sensor, the optical sensor, the temperature sensor and the switching element of the stretchable multimode sensor may include the amorphous metal, and thus the flexibility, life span and performance of the stretchable multimode sensor may be improved by the elasticity of the amorphous metal.

In the method of fabricating the stretchable multimode sensor according to the embodiments of the inventive concepts, the pressure sensor, the optical sensor, the temperature sensor and the switching element may be formed to include the amorphous metal of the same chemical element provided by the same process, and thus the process time and the process cost of the stretchable multimode sensor may be reduced.

While the inventive concepts have been described with reference to exemplary embodiments, the scopes of the inventive concepts are to be determined by the broadest permissible interpretation of the following claims and their equivalents, and shall not be restricted or limited by the foregoing description. In addition, it should be understood that it will be apparent to those skilled in the art that various changes and modifications may be made without departing from the spirits and scopes of the inventive concepts.

What is claimed is:

1. A method of fabricating an amorphous thin film, the method comprising:
   disposing a source including two or more kinds of metal chemical elements, and a substrate in a chamber; and
   performing a sputtering process to fabricate an amorphous thin film on the substrate from the source,
   wherein flexibility of the amorphous thin film is controlled by controlling a process pressure in the chamber,
   wherein the substrate is a polymer substrate, and
   wherein the polymer substrate is cooled or quenched after the fabrication of the amorphous thin film such that a wrinkle structure is generated at the amorphous thin film.

2. The method of claim 1, wherein the process pressure in the chamber is a minimum pressure which generates plasma in the chamber.

3. The method of claim 1, wherein a length of a void extending from a surface of the amorphous thin film in a depth direction is controlled depending on the process pressure in the chamber.

4. The method of claim 3, wherein the length of the void increases as the process pressure in the chamber increases, and wherein the length of the void decreases as the process pressure in the chamber decreases.

5. The method of claim 1, wherein the flexibility of the amorphous thin film decreases as the process pressure in the chamber increases, and wherein the flexibility of the amorphous thin film increases as the process pressure in the chamber decreases.

6. The method of claim 1, wherein a region in which a polymer of the polymer substrate is mixed with a metal of the amorphous thin film is provided at an interface between the polymer substrate and the amorphous thin film.

7. The method of claim 1, wherein the amorphous thin film includes an early transition metal and a late transition metal.

* * * * *